(12) United States Patent
Karnik et al.

(10) Patent No.: US 9,668,800 B2
(45) Date of Patent: Jun. 6, 2017

(54) METHODS AND SYSTEMS FOR TREATMENT OF SPASTICITY

(71) Applicant: MyoScience, Inc., Redwood City, CA (US)

(72) Inventors: Jwala Karnik, Santa Barbara, CA (US); Clint Carnell, Park City, UT (US); Jesse Rosen, Redwood City, CA (US); John Allison, Los Altos, CA (US)

(73) Assignee: MYOSCIENCE, INC., Fremont, CA (US)

( * ) Notice: Subject to any disclaimer, the term of this patent is extended or adjusted under 35 U.S.C. 154(b) by 404 days.

(21) Appl. No.: 14/218,925

(22) Filed: Mar. 18, 2014

(65) Prior Publication Data

US 2014/0276708 A1    Sep. 18, 2014

Related U.S. Application Data

(60) Provisional application No. 61/800,478, filed on Mar. 15, 2013.

(51) Int. Cl.
*A61B 18/02* (2006.01)
*A61B 18/00* (2006.01)

(52) U.S. Cl.
CPC .......... *A61B 18/02* (2013.01); *A61B 18/0218* (2013.01); *A61B 2018/00041* (2013.01);
(Continued)

(58) Field of Classification Search
CPC ................ A61B 18/02; A61B 18/0218; A61B 2018/0293; A61B 2018/00041;
(Continued)

(56) References Cited

U.S. PATENT DOCUMENTS 2,319,542 A    5/1943    Hall
2,672,032 A    3/1964    Towse
(Continued)

FOREIGN PATENT DOCUMENTS

CA    2643474 A1    9/2007
EP    0043447 A2    6/1981
(Continued)

OTHER PUBLICATIONS

Non-final Office Action for U.S. Appl. No. 14/025,527 mailed on Jun. 24, 2015, 11 pages.
(Continued)

*Primary Examiner* — Thomas Giuliani
(74) *Attorney, Agent, or Firm* — Kilpatrick, Townsend and Stockton, LLP

(57) ABSTRACT

A system for alleviating spasticity of a skeletal muscle having an associated motor nerve. The system may include a needle probe having at least one needle. The at least one needle has a proximal end, a distal end, and a needle lumen therebetween. The needle is configured for insertion proximate to the nerve. A cooling fluid supply lumen can extend distally within the needle lumen to a distal portion of the needle lumen. A cooling fluid source is couplable to the cooling fluid supply lumen to direct cooling fluid flow into the needle lumen. A controller having at least one processor configured to implement a spasticity treatment algorithm for controlling the cooling fluid source so that liquid from the cooling flow vaporizes within the needle lumen to provide a treatment phase to the motor nerve such spasticity of the skeletal muscle is mitigated.

18 Claims, 14 Drawing Sheets

(52) U.S. Cl.
CPC ............ *A61B 2018/00321* (2013.01); *A61B 2018/00625* (2013.01); *A61B 2018/00642* (2013.01); *A61B 2018/00839* (2013.01); *A61B 2018/0293* (2013.01)

(58) Field of Classification Search
CPC .. A61B 2018/0044; A61B 2018/00434; A61B 2018/00446; A61B 2018/0262; A61B 2018/00321
USPC .............................. 606/20–26; 607/109, 117
See application file for complete search history.

(56) References Cited

U.S. PATENT DOCUMENTS

| | | | |
|---|---|---|---|
| 3,266,492 A | 8/1966 | Steinberg | |
| 3,289,424 A | 12/1966 | Lee | |
| 3,343,544 A | 9/1967 | Dunn et al. | |
| 3,351,063 A | 11/1967 | Malaker et al. | |
| 3,439,680 A | 4/1969 | Thomas, Jr. | |
| 3,483,869 A | 12/1969 | Hayhurst | |
| 3,502,081 A | 3/1970 | Amoils | |
| 3,507,283 A | 4/1970 | Thomas, Jr. | |
| 3,532,094 A | 10/1970 | Stahl | |
| 3,664,344 A | 5/1972 | Bryne | |
| 3,702,114 A | 11/1972 | Zacarian | |
| 3,795,245 A | 3/1974 | Allen, Jr. et al. | |
| 3,814,095 A | 6/1974 | Lubens | |
| 3,830,239 A | 8/1974 | Stumpf et al. | |
| 3,886,945 A | 6/1975 | Stumpf et al. | |
| 3,889,681 A | 6/1975 | Waller et al. | |
| 3,951,152 A | 4/1976 | Crandell et al. | |
| 3,993,075 A | 11/1976 | Lisenbee et al. | |
| 4,140,109 A | 2/1979 | Savic et al. | |
| 4,207,897 A | 6/1980 | Lloyd et al. | |
| 4,236,518 A | 12/1980 | Floyd | |
| 4,306,568 A | 12/1981 | Torre | |
| 4,376,376 A | 3/1983 | Gregory | |
| 4,404,862 A | 9/1983 | Harris, Sr. | |
| 4,524,771 A | 6/1985 | McGregor et al. | |
| 4,758,217 A | 7/1988 | Gueret | |
| 4,802,475 A | 2/1989 | Weshahy | |
| 4,946,460 A | 8/1990 | Merry et al. | |
| 5,059,197 A | 10/1991 | Urie et al. | |
| 5,200,170 A | 4/1993 | McDow | |
| 5,294,325 A | 3/1994 | Liu | |
| 5,334,181 A | 8/1994 | Rubinsky et al. | |
| 5,520,681 A | 5/1996 | Fuller et al. | |
| 5,571,147 A | 11/1996 | Sluijter et al. | |
| 5,647,868 A | 7/1997 | Chinn | |
| 5,747,777 A | 5/1998 | Matsuoka | |
| 5,755,753 A | 5/1998 | Knowlton | |
| 5,814,040 A | 9/1998 | Nelson et al. | |
| 5,860,970 A | 1/1999 | Goddard et al. | |
| 5,879,378 A | 3/1999 | Usui | |
| 5,899,897 A | 5/1999 | Rabin et al. | |
| 5,916,212 A | 6/1999 | Baust et al. | |
| 5,976,505 A | 11/1999 | Henderson | |
| 6,003,539 A | 12/1999 | Yoshihara | |
| 6,032,675 A | 3/2000 | Rubinsky | |
| 6,039,730 A | 3/2000 | Rabin et al. | |
| 6,041,787 A | 3/2000 | Rubinsky | |
| 6,139,545 A | 10/2000 | Utley et al. | |
| 6,141,985 A | 11/2000 | Cluzeau et al. | |
| 6,142,991 A | 11/2000 | Schatzberger | |
| 6,182,666 B1 | 2/2001 | Dobak, III | |
| 6,196,839 B1 | 3/2001 | Ross | |
| 6,238,386 B1 | 5/2001 | Mueller et al. | |
| 6,277,099 B1 | 8/2001 | Strowe et al. | |
| 6,277,116 B1 | 8/2001 | Utely et al. | |
| 6,363,730 B1 | 4/2002 | Thomas et al. | |
| 6,364,899 B1 * | 4/2002 | Dobak, III ............. | A61B 18/02 606/20 |
| 6,371,943 B1 | 4/2002 | Racz et al. | |
| 6,432,102 B2 | 8/2002 | Joye et al. | |
| 6,494,844 B1 | 12/2002 | Van Bladel et al. | |
| 6,503,246 B1 | 1/2003 | Har-Shai et al. | |
| 6,506,796 B1 | 1/2003 | Fesus et al. | |
| 6,546,935 B2 | 4/2003 | Hooven | |
| 6,551,309 B1 | 4/2003 | LePivert | |
| 6,562,030 B1 | 5/2003 | Abboud et al. | |
| 6,629,951 B2 | 10/2003 | Laufer et al. | |
| 6,648,880 B2 | 11/2003 | Chauvet et al. | |
| 6,669,688 B2 | 12/2003 | Svaasand et al. | |
| 6,672,095 B1 | 1/2004 | Luo | |
| 6,682,501 B1 | 1/2004 | Nelson et al. | |
| 6,706,037 B2 | 3/2004 | Zvuloni et al. | |
| 6,723,092 B2 | 4/2004 | Brown et al. | |
| 6,749,624 B2 | 6/2004 | Knowlton | |
| 6,761,715 B2 | 7/2004 | Carroll | |
| 6,764,493 B1 | 7/2004 | Weber et al. | |
| 6,786,901 B2 | 9/2004 | Joye et al. | |
| 6,786,902 B1 | 9/2004 | Rabin et al. | |
| 6,789,545 B2 | 9/2004 | Littrup et al. | |
| 6,840,935 B2 | 1/2005 | Lee | |
| 6,858,025 B2 | 2/2005 | Maurice | |
| 6,902,554 B2 | 6/2005 | Huttner | |
| 6,905,492 B2 | 6/2005 | Zvuloni et al. | |
| 6,960,208 B2 | 11/2005 | Bourne et al. | |
| 7,001,400 B1 | 2/2006 | Modesitt et al. | |
| 7,081,111 B2 | 7/2006 | Svaasand et al. | |
| 7,081,112 B2 | 7/2006 | Joye et al. | |
| 7,083,612 B2 | 8/2006 | Littrup et al. | |
| 7,195,616 B2 | 3/2007 | Diller et al. | |
| 7,217,939 B2 | 5/2007 | Johansson et al. | |
| 7,250,046 B1 | 7/2007 | Fallat | |
| 7,311,672 B2 | 12/2007 | Van Bladel et al. | |
| 7,367,341 B2 | 5/2008 | Anderson et al. | |
| 7,402,140 B2 | 7/2008 | Spero et al. | |
| 7,422,586 B2 | 9/2008 | Morris et al. | |
| 7,578,819 B2 | 8/2009 | Bleich et al. | |
| 7,641,679 B2 | 1/2010 | Joye et al. | |
| 7,653,438 B2 | 1/2010 | Deem et al. | |
| 7,713,266 B2 | 5/2010 | Elkins et al. | |
| 7,850,683 B2 | 12/2010 | Elkins et al. | |
| 7,862,558 B2 | 1/2011 | Elkins et al. | |
| 7,998,137 B2 | 8/2011 | Elkins et al. | |
| 8,298,216 B2 | 10/2012 | Burger et al. | |
| 8,409,185 B2 | 4/2013 | Burger et al. | |
| 8,715,275 B2 | 5/2014 | Burger et al. | |
| 8,722,065 B2 | 5/2014 | Ishibashi et al. | |
| 9,039,688 B2 | 5/2015 | Palmer, III et al. | |
| 2002/0010460 A1 | 1/2002 | Joye et al. | |
| 2002/0013602 A1 | 1/2002 | Huttner | |
| 2002/0045434 A1 | 4/2002 | Masoian et al. | |
| 2002/0049436 A1 | 4/2002 | Zvuloni et al. | |
| 2002/0068929 A1 | 6/2002 | Zvuloni | |
| 2002/0120260 A1 | 8/2002 | Morris et al. | |
| 2002/0120261 A1 | 8/2002 | Morris et al. | |
| 2002/0120263 A1 | 8/2002 | Brown et al. | |
| 2002/0128638 A1 | 9/2002 | Chauvet et al. | |
| 2002/0156469 A1 | 10/2002 | Yon et al. | |
| 2002/0183731 A1 | 12/2002 | Holland et al. | |
| 2002/0193778 A1 | 12/2002 | Alchas et al. | |
| 2003/0036752 A1 | 2/2003 | Joye et al. | |
| 2003/0109912 A1 | 6/2003 | Joye et al. | |
| 2003/0130575 A1 | 7/2003 | Desai | |
| 2003/0181896 A1 | 9/2003 | Zvuloni et al. | |
| 2003/0195436 A1 | 10/2003 | Van Bladel et al. | |
| 2003/0220635 A1 | 11/2003 | Knowlton et al. | |
| 2003/0220674 A1 | 11/2003 | Anderson et al. | |
| 2004/0024391 A1 | 2/2004 | Cytron et al. | |
| 2004/0082943 A1 | 4/2004 | Littrup et al. | |
| 2004/0092875 A1 | 5/2004 | Kochamba | |
| 2004/0122482 A1 | 6/2004 | Tung et al. | |
| 2004/0143252 A1 | 7/2004 | Hurst | |
| 2004/0162551 A1 | 8/2004 | Brown et al. | |
| 2004/0167505 A1 | 8/2004 | Joye et al. | |
| 2004/0191229 A1 | 9/2004 | Link et al. | |
| 2004/0204705 A1 | 10/2004 | Lafontaine | |
| 2004/0210212 A1 | 10/2004 | Maurice | |
| 2004/0215178 A1 | 10/2004 | Maurice | |
| 2004/0215294 A1 | 10/2004 | Littrup et al. | |
| 2004/0215295 A1 | 10/2004 | Littrup et al. | |

(56) References Cited

U.S. PATENT DOCUMENTS

| | | |
|---|---|---|
| 2004/0220497 A1 | 11/2004 | Findlay et al. |
| 2004/0220648 A1 | 11/2004 | Carroll |
| 2004/0225276 A1 | 11/2004 | Burgess |
| 2004/0243116 A1 | 12/2004 | Joye et al. |
| 2004/0267248 A1 | 12/2004 | Duong et al. |
| 2004/0267257 A1 | 12/2004 | Bourne et al. |
| 2005/0004563 A1 | 1/2005 | Racz et al. |
| 2005/0177147 A1 | 8/2005 | Vancelette et al. |
| 2005/0177148 A1 | 8/2005 | van der Walt et al. |
| 2005/0182394 A1 | 8/2005 | Spero et al. |
| 2005/0203505 A1 | 9/2005 | Megerman et al. |
| 2005/0203593 A1 | 9/2005 | Shanks et al. |
| 2005/0209565 A1 | 9/2005 | Yuzhakov et al. |
| 2005/0209587 A1 | 9/2005 | Joye et al. |
| 2005/0224086 A1 | 10/2005 | Nahon |
| 2005/0228288 A1 | 10/2005 | Hurst |
| 2005/0251103 A1 | 11/2005 | Steffen et al. |
| 2005/0261753 A1 | 11/2005 | Littrup et al. |
| 2005/0276759 A1 | 12/2005 | Roser et al. |
| 2005/0281530 A1 | 12/2005 | Rizoiu et al. |
| 2005/0283148 A1 | 12/2005 | Janssen et al. |
| 2006/0009712 A1 | 1/2006 | Van Bladel et al. |
| 2006/0015092 A1 | 1/2006 | Joye et al. |
| 2006/0069385 A1 | 3/2006 | Lafontaine et al. |
| 2006/0079914 A1 | 4/2006 | Modesitt et al. |
| 2006/0084962 A1 | 4/2006 | Joye et al. |
| 2006/0089688 A1 | 4/2006 | Panescu |
| 2006/0111732 A1 | 5/2006 | Gibbens et al. |
| 2006/0129142 A1 | 6/2006 | Reynolds |
| 2006/0142785 A1 | 6/2006 | Modesitt et al. |
| 2006/0173469 A1 | 8/2006 | Klein et al. |
| 2006/0189968 A1 | 8/2006 | Howlett et al. |
| 2006/0190035 A1 | 8/2006 | Hushka et al. |
| 2006/0200117 A1 | 9/2006 | Hermans |
| 2006/0212028 A1 | 9/2006 | Joye et al. |
| 2006/0212048 A1 | 9/2006 | Crainich |
| 2006/0223052 A1 | 10/2006 | MacDonald et al. |
| 2006/0224149 A1 | 10/2006 | Hillely |
| 2006/0258951 A1 | 11/2006 | Bleich et al. |
| 2007/0060921 A1 | 3/2007 | Janssen et al. |
| 2007/0088217 A1 | 4/2007 | Babaev |
| 2007/0129714 A1 | 6/2007 | Elkins et al. |
| 2007/0156125 A1 | 7/2007 | DeLonzor |
| 2007/0161975 A1 | 7/2007 | Goulko |
| 2007/0167943 A1 | 7/2007 | Janssen et al. |
| 2007/0167959 A1 | 7/2007 | Modesitt et al. |
| 2007/0179509 A1 | 8/2007 | Nagata et al. |
| 2007/0198071 A1 | 8/2007 | Ting et al. |
| 2007/0225781 A1 | 9/2007 | Saadat et al. |
| 2007/0255362 A1 | 11/2007 | Levinson et al. |
| 2007/0270925 A1 | 11/2007 | Levinson |
| 2008/0051775 A1 | 2/2008 | Evans |
| 2008/0051776 A1 | 2/2008 | Bliweis et al. |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0154254 A1 | 6/2008 | Burger et al. |
| 2008/0183164 A1* | 7/2008 | Elkins ............ A61B 18/02 606/21 |
| 2008/0200910 A1 | 8/2008 | Burger et al. |
| 2008/0287839 A1 | 11/2008 | Rosen et al. |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0118722 A1 | 5/2009 | Ebbers et al. |
| 2009/0171334 A1 | 7/2009 | Elkins et al. |
| 2009/0248001 A1 | 10/2009 | Burger et al. |
| 2009/0264876 A1 | 10/2009 | Roy et al. |
| 2009/0299357 A1* | 12/2009 | Zhou ............ A61B 18/02 606/21 |
| 2010/0114191 A1 | 5/2010 | Newman |
| 2010/0168725 A1 | 7/2010 | Babkin et al. |
| 2010/0305439 A1 | 12/2010 | Shai et al. |
| 2010/0331883 A1* | 12/2010 | Schmitz ............ A61B 10/0275 606/249 |
| 2011/0144631 A1 | 6/2011 | Elkins et al. |
| 2011/0196267 A1 | 8/2011 | Mishelevich |
| 2012/0065629 A1 | 3/2012 | Elkins et al. |
| 2012/0089211 A1 | 4/2012 | Curtis et al. |
| 2012/0259322 A1 | 10/2012 | Fourkas et al. |
| 2012/0265187 A1 | 10/2012 | Palmer, III et al. |
| 2013/0253605 A1 | 9/2013 | Bennett et al. |
| 2013/0324990 A1 | 12/2013 | Burger et al. |
| 2014/0249519 A1 | 9/2014 | Burger et al. |
| 2014/0276539 A1 | 9/2014 | Allison et al. |
| 2014/0343542 A1 | 11/2014 | Karnik et al. |
| 2014/0343543 A1 | 11/2014 | Karnik et al. |
| 2014/0343544 A1 | 11/2014 | Carnell et al. |

FOREIGN PATENT DOCUMENTS

| | | |
|---|---|---|
| EP | 0777123 A1 | 6/1997 |
| EP | 0955012 A1 | 11/1999 |
| EP | 1074273 A1 | 2/2001 |
| EP | 1377327 B1 | 9/2007 |
| EP | 1862125 A2 | 12/2007 |
| EP | 2 499 984 A1 | 9/2012 |
| GB | 1360353 B | 7/1974 |
| GB | 1402632 A | 8/1975 |
| JP | 60-013111 | 1/1985 |
| JP | H04-357945 A | 12/1992 |
| JP | 05-038347 | 2/1993 |
| JP | 10-014656 A | 1/1998 |
| JP | 2001-178737 A | 7/2001 |
| JP | 2005-080988 A | 3/2005 |
| JP | 2006-130055 A | 5/2006 |
| JP | 2008-515469 A | 5/2008 |
| RU | 2254060 | 6/2005 |
| WO | 97/49344 A1 | 12/1997 |
| WO | 01/97702 A1 | 12/2001 |
| WO | 02/02026 A1 | 1/2002 |
| WO | 02/092153 A2 | 11/2002 |
| WO | 2004/039440 A1 | 5/2004 |
| WO | 2004/045434 A2 | 6/2004 |
| WO | 2004/089460 A2 | 10/2004 |
| WO | 2005/000106 A2 | 1/2005 |
| WO | 2005/079321 A2 | 9/2005 |
| WO | 2005/096979 A1 | 10/2005 |
| WO | 2006/012128 A2 | 2/2006 |
| WO | 2006/023348 A1 | 3/2006 |
| WO | 2006/044727 A2 | 4/2006 |
| WO | 2006/062788 A2 | 6/2006 |
| WO | 2006/125835 A1 | 11/2006 |
| WO | 2006/127467 A2 | 11/2006 |
| WO | 2007/025106 A2 | 3/2007 |
| WO | 2007/037326 A1 | 4/2007 |
| WO | 2007/089603 A2 | 8/2007 |
| WO | 2007/109656 A2 | 9/2007 |
| WO | 2007/129121 A1 | 11/2007 |
| WO | 2007/135629 A1 | 11/2007 |
| WO | 2009/026471 A1 | 2/2009 |
| WO | 2010/075438 A1 | 7/2010 |
| WO | 2010/075448 A1 | 7/2010 |
| WO | 2014/146105 A2 | 9/2014 |
| WO | 2014/146106 A2 | 9/2014 |
| WO | 2014/146122 A1 | 9/2014 |
| WO | 2014/146127 A1 | 9/2014 |

OTHER PUBLICATIONS

Invitation to Pay Additional Fees and, Where Applicable, Protest Fee with Partial International Search Report mailed Aug. 5, 2014, from PCT Application No. PCT/US2014/031081 (2 pages).
International Search Report and Written Opinion mailed Sep. 4, 2014, from PCT Application No. PCT/US2014/031079 (16 pages).
International Search Report and Written Opinion mailed Aug. 8, 2014, from PCT Application No. PCT/US2014/031107 (16 pages).
International Search Report and Written Opinion mailed Aug. 8, 2014, from PCT Application No. PCT/US2014/031113 (14 pages).
Bohannon et al., Interrater reliability of a modified Ashworth scale of muscle spasticity, Physical Therapy, 67(2): 206, 1987, 4 pages.

(56) References Cited

OTHER PUBLICATIONS

Boyd et al., "Objective measurement of clinical findings in the use of botulinum toxin type A for the management of children with cerebral palsy", European Journal of Neurology, 6: s23-s35, 1999, 13 pages.

Farrar et al., "Validity, reliability, and clinical importance of change in a 0-10 numeric rating scale measure of spasticity; a post hoc analysis of a randomized, double-blind, placebo-controlled trial", Clinical Therapeutics, 30:5: 974-985, 2008, 12 pages.

Gallagher et al., "Prospective validation of clinically important changes in pain severity measured on visual analog scale", Annals of Emergency Medicine, 38:6;633-638, 2001, 6 pages.

Morris, "Ashworth and Tardieu scales: Their clinical relevance for measuring spasticity in adult and paediatric neurological populations", Physical Therapy Reviews, 7: 53-62, 2002, 10 pages.

Page et al., "Clinically important differences for the upper-extremity Fugl-Meyer scale in people with minimal to moderate impairment due to chronic stroke", Physical Therapy, 92: 791-798, 2012, 10 pages.

Penn et al., "Intrathecal baclofen for severe spinal spasticity", The New England Journal of Medicine, Jun. 8, 1989;320(23):1517-21, 5 pages.

Shaw et al., "BoTULS: a multicentre randomised controlled trial to evaluate the clinical effectiveness and cost-effectiveness of treating upper limb spasticity due to stroke with botulinum toxin type A", Health Technology Assessment; 14:26, 2010, 158 pages.

Sullivan et al., "Fugl-Meyer assessment of sensorimotor function after stroke: Standardized training procedure for clinical practice and clinical trials", Stroke. 2011; 42:427-432, 27 pages.

U.S. Appl. No. 61/116,050, filed Nov. 19, 2008 by Holland et al., 46 pages (expired).

U.S. Appl. No. 14/025,527, filed Sep. 12, 2013 by Allison et al.
U.S. Appl. No. 14/218,146, filed Mar. 18, 2014 by Karnik et al.
U.S. Appl. No. 14/218,167, filed Mar. 18, 2014 by Karnik et al.
U.S. Appl. No. 14/218,901, filed Mar. 18, 2014 by Carnell et al.

Notification of Transmittal of the International Search Report and the Written Opinion of the International Searching Authority, or the Declaration; International Search Report and the Written Opinion of the International Searching Authority for corresponding International Patent Application No. PCT/US2014/031081 mailed on Oct. 29, 2014, 14 pages.

Advanced Cosmetic Intervention, Inc. [webpage], retrieved from the Internet: <<http://www.acisurgery.com>>, copyright 2007, 1 page.

Cryopen, LLC [Press Release], "CyroPen, LLC Launches Revolutionary, State-of-the-Art Medical Device—The Dure of Cryosurgery in a Pend," dated Apr. 27, 2007, retrieved from the Internet: <<http://cryopen.com/press.htm>>, 3 pages total.

Cryopen, LLC., [webpage], retrieved from the Internet: <<http://cryopen.com/>>, copyright 2006-2008, 2 pages total.

Cryosurgical Concepts, Inc., [webpage] "CryoProbe™", retrieved from the Internet: << http://www.cryo-surgical.com//>> on Feb. 8, 2008, 2 pages total.

Dasiou-Plankida, "Fat injections for facial rejuvenation: 17 years experience in 1720 patients," Journal of Cosmetic Dermatology, Oct. 22, 2004; 2(3-4): 119-125.

Foster et al., "Radiofrequency Ablation of Facial Nerve Branches Controlling Glabellar Frowning", Dermatol Surg. Dec. 2009; 35(12):1908-1917.

Har-Shai et al., "Effect of skin surface temperature on skin pigmentation during contact and intralesional cryosurgery of hypertrophic scars and Kleoids," Journal of the European Academy of Dermatology and Venereology, Feb. 2007, vol. 21, issue 2, pp. 191-198.

Magalov et al., "Isothermal volume contours generated in a freezing gel by embedded cryo-needles with applications to cryo-surgery," Cryobiology Oct. 2007, 55(2):127-137.

Metrum CryoFlex, Cryoablation in pain management brochure, 2012, 5 pages.

Metrum CryoFlex, Cryosurgery probes and accessories catalogue, 2009, 25 pages.

One Med Group, LLC., [webpage] "CryoProbe™", retrieved from the Internet: <<http://www.onemedgroup.com/>> on Feb. 4, 2008, 2 pages total.

Rewcastle et al., "A model for the time dependent three-dimensional thermal distribution within iceballs surrounding multiple cryoprobes," Med Phys. Jun. 2001;28(6):1125-1137.

Rutkove, "Effects of Temperature on Neuromuscular Electrophysiology," Muscles and Nerves, Jun. 12, 2001; 24(7):867-882; retrieved from http://www3.interscience.wiley.com/cgi-bin/fulltext/83502418/PDFSTART.

Utley et al., "Radiofrequency Ablation of the Nerve to the Corrugator Muscle for the Elimination of Glabellar Furrowing," Arch. Facial Plastic Surgery 1:46-48, 1999.

Yang et al., "Apoptosis induced by cryo-injury in human colorectal cancer cells is associated with mitochondrial dysfunction.," International Journal of Cancer, 2002, vol. 103, No. 3, pp. 360-369.

* cited by examiner

METHODS AND SYSTEMS FOR TREATMENT OF SPASTICITY

CROSS-REFERENCES TO RELATED APPLICATIONS

This application claims benefit of U.S. Provisional Patent Application No. 61/800,478, filed Mar. 15, 2013, which is incorporated by reference.

BACKGROUND OF THE INVENTION

Spasticity, common in neurological disorders, is part of the upper motor neuron syndrome displaying increased tone, clonus, spasms, spastic dystonia and co-contractions. The impact of spasticity on the patient varies from a subtle neurological sign to severe spasticity causing pain and contractures. Upper limb spasticity (ULS) is the rapid contraction or shortening of the muscles in the arm causing abnormal muscle movements in the elbow, wrist and fingers. It has been reported that over 1 million Americans with traumatic injury to the brain or spinal cord, stroke, multiple sclerosis and cerebral palsy experience ULS. Tightly clenched fists, twisted wrist and elbow joints, and fixed arms in flexed positions result in extreme discomfort, pain and spasm. These symptoms may be aggravated by fatigue, stress, infections, and pain. Additionally, spasticity may lead to increased fatigue due to the extra energy expended to overcome tone during the movements involved in daily living activities.

Spasticity often requires both pharmacological and non-pharmacological interventions. The most commonly used pharmacological intervention is Baclofen, a muscle relaxant that works on nerves in the spinal cord. Oral Baclofen is commonly administered intrathecally through an implanted pumped and is often administered in conjunction with Botulinum toxin (Botox) and neurolytics (phenol) injections. Common side effects associated with Baclofen are drowsiness and muscle weakness. Furthermore, implanted pumps may cause post-implant complications including pump failure, infection, and lead displacement. While both Botulinum toxin and neurolytic injections have been shown to be effective in relieving spasticity both alone and in conjunction with oral interventions, both solutions are short-term and require retreatment every 3-6 months. Neurolytic injections impair nerve conduction by destroying a portion of a nerve and often cause additional necrosis of the neighboring sensory nerves, skin, muscles, blood vessels, and other soft tissues. In more severe cases, surgery can be performed to section nerves and relieve spasticity. These surgical procedures typically reduce upper-extremity spasticity but are associated with more severe, long-term adverse effects such as sensory disturbance and decrease in motor function in the affected area. It is clear that a nonsurgical, minimally invasive, effective approach to pain associated with ULS is desirable.

BRIEF SUMMARY OF THE INVENTION

Embodiments of the invention relate to a system for alleviating spasticity of a skeletal muscle having an associated motor nerve. The system may include a needle probe having at least one needle, the at least one needle having a proximal end, a distal end, and a needle lumen therebetween, the needle configured for insertion proximate to the nerve. A cooling fluid supply lumen can extend distally within the needle lumen to a distal portion of the needle lumen. A cooling fluid source is couplable to the cooling fluid supply lumen to direct cooling fluid flow into the needle lumen. A controller having at least one processor configured to implement a spasticity treatment algorithm for controlling the cooling fluid source so that liquid from the cooling flow vaporizes within the needle lumen to provide a treatment to the motor nerve such spasticity of the skeletal muscle is mitigated.

Embodiments of the invention relate to a system for a method for alleviating spasticity of a skeletal muscle having an associated motor nerve. In the method a distal end of a cryogenic cooling needle probe is positioned proximal to the motor nerve. The needle probe has at least one needle with a lumen. A treatment is delivered to the target tissue with the cryogenic cooling needle, the treatment comprising a cooling phase where cooling fluid flows into the needle lumen so that liquid from the cooling flow vaporizes within the needle lumen to provide cooling to the nerve such that spasticity of the skeletal muscle is mitigated.

In many embodiments, a heating element coupled with a proximal portion of the needle, the heating element configured to deliver heating phases to the skin of the patient; and the processor is configured to control the cooling fluid flow and the heating element in response to operator input, the processor configured to provide the treatment in response to the operator input, the treatment comprising at least one heating phase and one cooling phase.

In many embodiments, the processor is further configured to provide a degree of skin warmer throughout the treatment phase.

In many embodiments, the degree of skin warmer comprises 28-42° C. skin warmer throughout the treatment phase.

In many embodiments, the at least one heating phase comprises a pre-heat phase with the heating element before the at least one cooling phase.

In many embodiments, the pre-heat phase has a duration of 10-20 seconds.

In many embodiments, the at least one cooling phase has a duration of 15-120 seconds.

In many embodiments, the at least one heating phase further comprises a post-heat phase.

In many embodiments, the post-heat phase has a duration of 5-15 seconds.

In many embodiments, the at least one needle comprises a length of 10-20 mm.

In many embodiments, the needle probe includes three needles.

In many embodiments, the needle probe includes a plurality of needles spaced apart from another by 5-8 mm.

In many embodiments, the spasticity treatment algorithm is configured to cause the needle probe to generate a cryozone having a volume of 65-125 mm$^3$.

In many embodiments, one or a combination of transcutaneous electrical nerve stimulation, percutaneous electrical nerve stimulation, and ultrasound is used to locate the motor nerve.

DETAILED DESCRIPTION OF THE INVENTION

The present invention provides improved medical devices, systems, and methods. Embodiments of the invention may facilitate remodeling of target tissues disposed at and below the skin, optionally treat spasticity of a skeletal muscle by remodeling tissue of a motor nerve. Embodiments of the invention may utilize a handheld refrigeration system that can use a commercially available cartridge of fluid refrigerant. Refrigerants well suited for use in handheld refrigeration systems may include nitrous oxide and carbon dioxide. These can achieve temperatures approaching −90° C.

Motor nerves and associated tissues may be temporarily immobilized using moderately cold temperatures of 10° C. to −5° C. without permanently disabling the tissue structures. Using an approach similar to that employed for identifying structures associated with atrial fibrillation, a needle probe or other treatment device can be used to identify a target tissue structure in a diagnostic mode with these moderate temperatures, and the same probe (or a different probe) can also be used to provide a longer term or permanent treatment, optionally by ablating the target tissue zone and/or inducing apoptosis at temperatures from about −5° C. to about −50° C. In some embodiments, apoptosis may be induced using treatment temperatures from about −1° C. to about −15° C., or from about −1° C. to about −19° C., optionally so as to provide a longer lasting treatment that limits or avoids inflammation and mobilization of skeletal muscle satellite repair cells. In some embodiments, axonotmesis with Wallerian degeneration of a nerve is desired, which may be induced using treatment temperatures from about −20° C. to about −100° C. Hence, the duration of the treatment efficacy of such subdermal cryogenic treatments may be selected and controlled, with colder temperatures, longer treatment times, and/or larger volumes or selected patterns of target tissue determining the longevity of the treatment. Additional description of cryogenic cooling methods and devices may be found in commonly assigned U.S. Pat. No. 7,713,266 entitled "Subdermal Cryogenic Remodeling of Muscle, Nerves, Connective Tissue, and/or Adipose Tissue (Fat)", U.S. Pat. No. 7,850,683 entitled "Subdermal Cryogenic Remodeling of Muscles, Nerves, Connective Tissue, and/or Adipose Tissue (Fat)", U.S. patent application Ser. No. 13/325,004 entitled "Method for Reducing Hyperdynamic Facial Wrinkles", and U.S. Pub. No. 2009/0248001 entitled "Pain Management Using Cryogenic Remodeling," the full disclosures of which are each incorporated by reference herein.

1. CRYOGENIC SYSTEMS FOR TREATING SPASTICITY

Figure 1A:
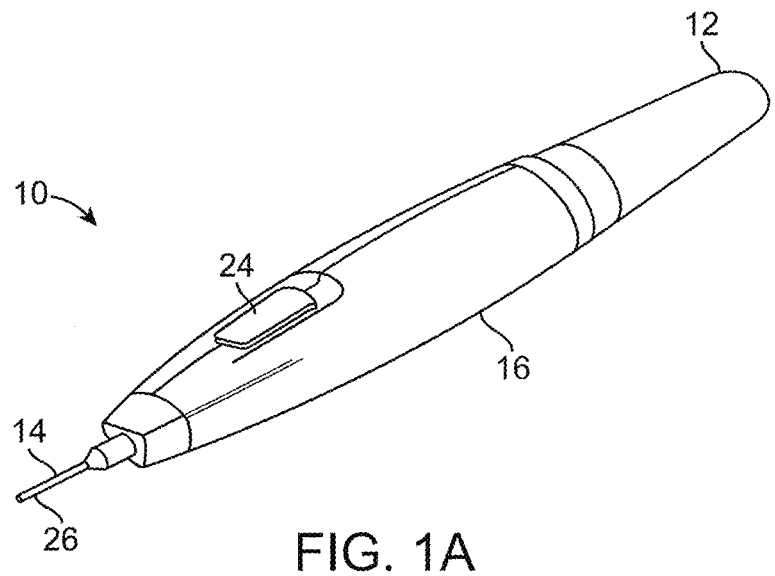
FIG. 1A is a perspective view of a self-contained subdermal cryogenic remodeling probe and system, according to some embodiments of the invention.
Figure 1B:
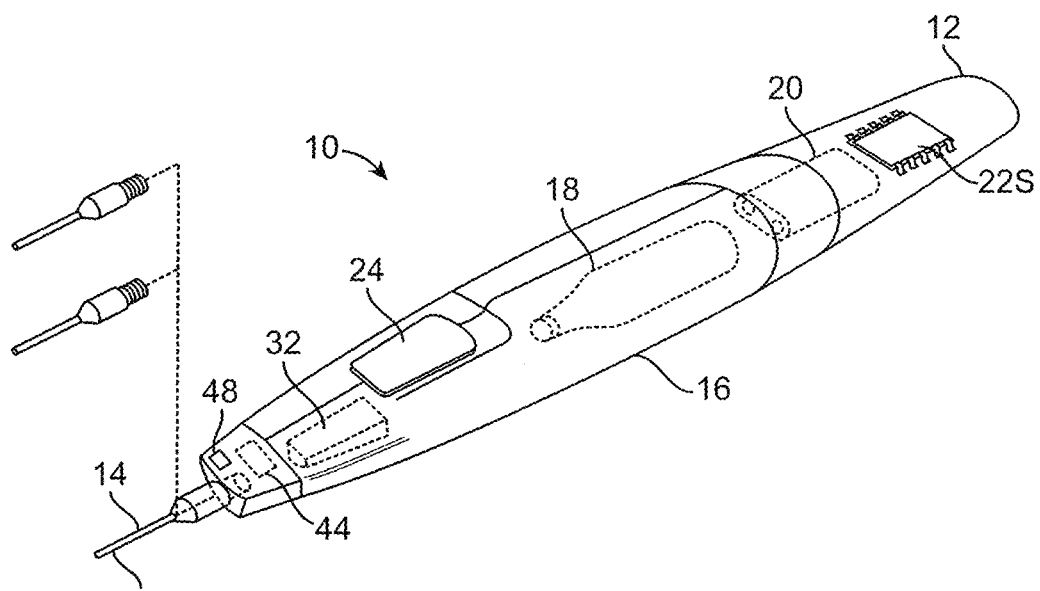
FIG. 1B is a partially transparent perspective view of the self-contained probe of FIG. 1A, showing internal components of the cryogenic remodeling system and schematically illustrating replacement treatment needles for use with the disposable probe according to some embodiments of the invention.

Referring now to FIGS. 1A and 1B, a system for cryogenic remodeling here comprises a self-contained probe handpiece generally having a proximal end 12 and a distal end 14. A handpiece body or housing 16 has a size and ergonomic shape suitable for being grasped and supported in a surgeon's hand or other system operator. As can be seen most clearly in FIG. 1B, a cryogenic cooling fluid supply 18, a supply valve 32 and electrical power source 20 are found within housing 16, along with a circuit 22 having a processor for controlling cooling applied by self-contained system 10 in response to actuation of an input 24. Alternatively, electrical power can be applied through a cord from a remote power source. Power source 20 also supplies power to heater element 44 in order to heat the proximal region of probe 26 which may thereby help to prevent unwanted skin damage, and a temperature sensor 48 adjacent the proximal region of probe 26 helps monitor probe temperature. Additional details on the heater 44 and temperature sensor 48 are described in greater detail below. When actuated, supply valve 32 controls the flow of cryogenic cooling fluid from fluid supply 18. Some embodiments may, at least in part, be manually activated, such as through the use of a manual supply valve and/or the like, so that processors, electrical power supplies, and the like may not be required.

Extending distally from distal end 14 of housing 16 may be a tissue-penetrating cryogenic cooling probe 26. Probe 26 is thermally coupled to a cooling fluid path extending from cooling fluid source 18, with the exemplary probe comprising a tubular body receiving at least a portion of the cooling fluid from the cooling fluid source therein. The exemplary probe 26 may comprise a 30 g needle having a sharpened distal end that is axially sealed. Probe 26 may have an axial length between distal end 14 of housing 16 and the distal end of the needle of between about 0.5 mm and 15 cm, preferably having a length from about 3 mm to about 10 mm. Such needles may comprise a stainless steel tube with an inner diameter of about 0.006 inches and an outer diameter of about 0.012 inches, while alternative probes may comprise structures having outer diameters (or other lateral cross-sectional dimensions) from about 0.006 inches to about 0.100 inches. Generally, needle probe 26 may comprise a 16 g or smaller size needle, often comprising a 20 g needle or smaller, typically comprising a 25, 26, 27, 28, 29, or 30 g or smaller needle.

In some embodiments, probe 26 may comprise two or more needles arranged in a linear array, such as those disclosed in previously incorporated U.S. Pat. No. 7,850,683. Another exemplary embodiment of a probe having multiple needle probe configurations allow the cryogenic treatment to be applied to a larger or more specific treatment area. Other needle configurations that facilitate controlling the depth of needle penetration and insulated needle embodiments are disclosed in commonly assigned U.S. Patent Publication No. 2008/0200910 entitled "Replaceable and/or Easily Removable Needle Systems for Dermal and Transdermal Cryogenic Remodeling," the entire content of which is incorporated herein by reference. Multiple needle arrays may also be arrayed in alternative configurations such as a triangular or square array.

Arrays may be designed to treat a particular region of tissue, or to provide a uniform treatment within a particular region, or both. In some embodiments needle 26 may be releasably coupled with body 16 so that it may be replaced after use with a sharper needle (as indicated by the dotted line) or with a needle having a different configuration. In exemplary embodiments, the needle may be threaded into the body, press fit into an aperture in the body or have a quick disconnect such as a detent mechanism for engaging the needle with the body. A quick disconnect with a check valve may be advantageous since it may permit decoupling of the needle from the body at any time without excessive coolant discharge. This can be a useful safety feature in the event that the device fails in operation (e.g. valve failure), allowing an operator to disengage the needle and device from a patient's tissue without exposing the patient to coolant as the system depressurizes. This feature may also be advantageous because it allows an operator to easily exchange a dull needle with a sharp needle in the middle of a treatment. One of skill in the art will appreciate that other coupling mechanisms may be used.

Addressing some of the components within housing 16, the exemplary cooling fluid supply 18 may comprise a canister, sometimes referred to herein as a cartridge, containing a liquid under pressure, with the liquid preferably having a boiling temperature of less than 37° C. at one atmosphere of pressure. When the fluid is thermally coupled to the tissue-penetrating probe 26, and the probe is positioned within the patient so that an outer surface of the probe is adjacent to a target tissue, the heat from the target tissue evaporates at least a portion of the liquid and the enthalpy of vaporization cools the target tissue. A supply valve 32 may be disposed along the cooling fluid flow path between canister 18 and probe 26, or along the cooling fluid path after the probe so as to limit coolant flow thereby regulating the temperature, treatment time, rate of temperature change, or other cooling characteristics. The valve will often be powered electrically via power source 20, per the direction of processor 22, but may at least in part be manually powered. The exemplary power source 20 comprises a rechargeable or single-use battery. Additional details about valve 32 are disclosed below and further disclosure on the power source 20 may be found in commonly assigned Int'l Pub. No. WO 2010/075438 entitled "Integrated Cryosurgical Probe Package with Fluid Reservoir and Limited Electrical Power Source," the entire contents of which are incorporated herein by reference.

The exemplary cooling fluid supply 18 may comprise a single-use canister. Advantageously, the canister and cooling fluid therein may be stored and/or used at (or even above) room temperature. The canister may have a frangible seal or may be refillable, with the exemplary canister containing liquid nitrous oxide, $N_2O$. A variety of alternative cooling fluids might also be used, with exemplary cooling fluids including fluorocarbon refrigerants and/or carbon dioxide. The quantity of cooling fluid contained by canister 18 will typically be sufficient to treat at least a significant region of a patient, but will often be less than sufficient to treat two or more patients. An exemplary liquid $N_2O$ canister might contain, for example, a quantity in a range from about 1 gram to about 40 grams of liquid, more preferably from about 1 gram to about 35 grams of liquid, and even more preferably from about 7 grams to about 30 grams of liquid.

Processor 22 will typically comprise a programmable electronic microprocessor embodying machine readable computer code or programming instructions for implementing one or more of the treatment methods described herein. The microprocessor will typically include or be coupled to a memory (such as a non-volatile memory, a flash memory, a read-only memory ("ROM"), a random access memory ("RAM"), or the like) storing the computer code and data to be used thereby, and/or a recording media (including a magnetic recording media such as a hard disk, a floppy disk, or the like; or an optical recording media such as a CD or DVD) may be provided. Suitable interface devices (such as digital-to-analog or analog-to-digital converters, or the like) and input/output devices (such as USB or serial I/O ports, wireless communication cards, graphical display cards, and the like) may also be provided. A wide variety of commercially available or specialized processor structures may be used in different embodiments, and suitable processors may make use of a wide variety of combinations of hardware and/or hardware/software combinations. For example, processor 22 may be integrated on a single processor board and may run a single program or may make use of a plurality of boards running a number of different program modules in a wide variety of alternative distributed data processing or code architectures.

Figure 2A:
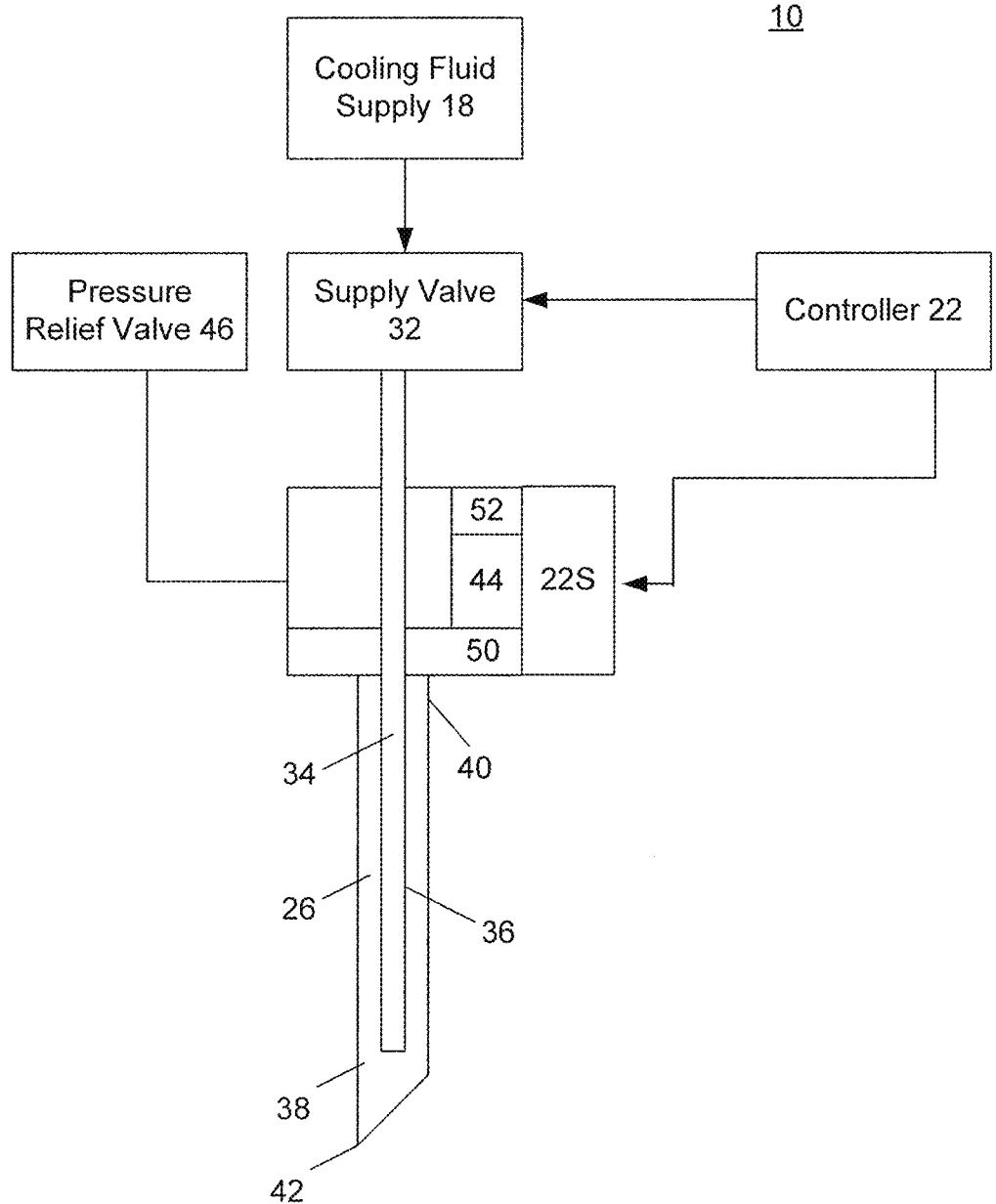
FIG. 2A schematically illustrates exemplary components that may be included in the treatment system.

Referring now to FIG. 2A, schematic 11 shows a simplified diagram of cryogenic cooling fluid flow and control. The flow of cryogenic cooling fluid from fluid supply 18 may be controlled by a supply valve 32. Supply valve 32 may comprise an electrically actuated solenoid valve, a motor actuated valve or the like operating in response to control signals from controller 22, and/or may comprise a manual valve. Exemplary supply valves may comprise structures suitable for on/off valve operation, and may provide venting of the fluid source and/or the cooling fluid path downstream of the valve when cooling flow is halted so as to limit residual cryogenic fluid vaporization and cooling. Additionally, the valve may be actuated by the controller in order to modulate coolant flow to provide high rates of cooling in some instances where it is desirable to promote necrosis of tissue such as in malignant lesions and the like or slow cooling which promotes ice formation between cells rather than within cells when necrosis is not desired. More complex flow modulating valve structures might also be used in other embodiments. For example, other applicable valve embodiments are disclosed in previously incorporated U.S. Pub. No. 2008/0200910.

Still referring to FIG. 2A, an optional heater (not illustrated) may be used to heat cooling fluid supply 18 so that heated cooling fluid flows through valve 32 and through a lumen 34 of a cooling fluid supply tube 36. In some embodiments a safety mechanism can be included so that the cooling supply is not overheated. Examples of such embodiments are disclosed in commonly assigned International Publication No. WO 2010075438, the entirety of which is incorporated by reference herein.

Supply tube 36 is, at least in part, disposed within a lumen 38 of needle 26, with the supply tube extending distally from a proximal end 40 of the needle toward a distal end 42. The exemplary supply tube 36 comprises a fused silica tubular structure (not illustrated) having a polymer coating and extending in cantilever into the needle lumen 38. Supply tube 36 may have an inner lumen with an effective inner diameter of less than about 200 µm, the inner diameter often being less than about 100 µm, and typically being less than about 40 µm. Exemplary embodiments of supply tube 36 have inner lumens of between about 15 and 50 µm, such as about 30 µm. An outer diameter or size of supply tube 36 will typically be less than about 1000 µm, often being less than about 800 µm, with exemplary embodiments being between about 60 and 150 µm, such as about 90 µm or 105 µm. The tolerance of the inner lumen diameter of supply tubing 36 will preferably be relatively tight, typically being about +/−10 µm or tighter, often being +/−5 µm or tighter, and ideally being +/−3 µm or tighter, as the small diameter supply tube may provide the majority of (or even substantially all of) the metering of the cooling fluid flow into needle 26. Additional details on various aspects of needle 26 along with alternative embodiments and principles of operation are disclosed in greater detail in U.S. Patent Publication No. 2008/0154254 entitled "Dermal and Transdermal Cryogenic Microprobe Systems and Methods," the entire contents of which are incorporated herein by reference. Previously incorporated U.S. Patent Publication No. 2008/0200910 also discloses additional details on the needle 26 along with various alternative embodiments and principles of operation.

The cooling fluid injected into lumen 38 of needle 26 will typically comprise liquid, though some gas may also be injected. At least some of the liquid vaporizes within needle 26, and the enthalpy of vaporization cools the needle and also the surrounding tissue engaged by the needle. An optional heater 44 (illustrated in FIG. 1B) may be used to heat the proximal region of the needle in order to prevent unwanted skin damage in this area, as discussed in greater detail below. Controlling a pressure of the gas/liquid mixture within needle 26 substantially controls the temperature within lumen 38, and hence the treatment temperature range of the tissue. A relatively simple mechanical pressure relief valve 46 may be used to control the pressure within the lumen of the needle, with the exemplary valve comprising a valve body such as a ball bearing, urged against a valve seat by a biasing spring. An exemplary relief valve is disclosed in U.S. Provisional Patent Application No. 61/116,050 previously incorporated herein by reference. Thus, the relief valve may allow better temperature control in the needle, minimizing transient temperatures. Further details on exhaust volume are disclosed in previously incorporated U.S. Pat. Pub. No. 2008/0200910.

The heater 44 may be thermally coupled to a thermally responsive element 50, which is supplied with power by the controller 22 and thermally coupled to a proximal portion of the needle 26. The thermally responsive element 50 can be a block constructed from a material of high thermal conductivity and low heat capacity, such as aluminum. A first temperature sensor 52 (e.g., thermistor, thermocouple) can also be thermally coupled the thermally responsive element 50 and communicatively coupled to the controller 22. A second temperature sensor 53 can also be positioned near the heater 44, for example, such that the first temperature sensor 52 and second temperature sensor 53 are placed in different positions within the thermally responsive element 50. In some embodiments, the second temperature sensor 53 is placed closer to a tissue contacting surface than the first temperature sensor 52 is placed in order to provide comparative data (e.g., temperature differential) between the sensors 52, 53. The controller 22 can be configured to receive temperature information of the thermally responsive element 50 via the temperature sensor 52 in order to provide the heater 44 with enough power to maintain the thermally responsive element 50 at a particular temperature.

The controller 22 can be further configured to monitor power draw from the heater 44 in order to characterize tissue type, perform device diagnostics, and/or provide feedback for a tissue treatment algorithm. This can be advantageous over monitoring temperature alone, since power draw from the heater 44 can vary greatly while temperature of the thermally responsive element 50 remains relatively stable. For example, during treatment of target tissue, maintaining the thermally responsive element 50 at 40° C. during a cooling phase may take 1.0 W initially (for a needle <10 mm in length) and is normally expected to climb to 1.5 W after 20 seconds, due to the needle 26 drawing in surrounding heat. An indication that the heater is drawing 2.0 W after 20 seconds to maintain 40° C. can indicate that an aspect of the system 10 is malfunctioning and/or that the needle 26 is incorrectly positioned. Correlations with power draw and correlated device and/or tissue conditions can be determined experimentally to determine acceptable treatment power ranges.

In some embodiments, it may be preferable to limit frozen tissue that is not at the treatment temperature, i.e., to limit the size of a formed cooling zone within tissue. Such cooling zones may be associated with a particular physical reaction, such as the formation of an ice-ball, or with a particular temperature profile or temperature volume gradient required to therapeutically affect the tissue therein. To achieve this, metering coolant flow could maintain a large thermal gradient at its outside edges. This may be particularly advantageous in applications for creating an array of connected cooling zones (i.e., fence) in a treatment zone, as time would be provided for the treatment zone to fully develop within the fenced in portion of the tissue, while the outer boundaries maintained a relatively large thermal gradient due to the repeated application and removal of refrigeration power. This could provide a mechanism within the body of tissue to thermally regulate the treatment zone and could provide increased ability to modulate the treatment zone at a prescribed distance from the surface of the skin. A related treatment algorithm could be predefined, or it could be in response to feedback from the tissue.

Such feedback could be temperature measurements from the needle 26, or the temperature of the surface of the skin could be measured. However, in many cases monitoring temperature at the needle 26 is impractical due to size constraints. To overcome this, operating performance of the sensorless needle 26 can be interpolated by measuring characteristics of thermally coupled elements, such as the thermally responsive element 50.

Additional methods of monitoring cooling and maintaining an unfrozen portion of the needle include the addition of a heating element and/or monitoring element into the needle itself. This could consist of a small thermistor or thermocouple, and a wire that could provide resistive heat. Other power sources could also be applied such as infrared light, radiofrequency heat, and ultrasound. These systems could also be applied together dependent upon the control of the treatment zone desired.

Alternative methods to inhibit excessively low transient temperatures at the beginning of a refrigeration cycle might be employed instead of or together with the limiting of the exhaust volume. For example, the supply valve 32 might be cycled on and off, typically by controller 22, with a timing sequence that would limit the cooling fluid flowing so that only vaporized gas reached the needle lumen 38 (or a sufficiently limited amount of liquid to avoid excessive dropping of the needle lumen temperature). This cycling might be ended once the exhaust volume pressure was sufficient so that the refrigeration temperature would be within desired limits during steady state flow. Analytical models that may be used to estimate cooling flows are described in greater detail in previously incorporated U.S. Patent Pub. No. 2008/0154254.

Figure 2B:
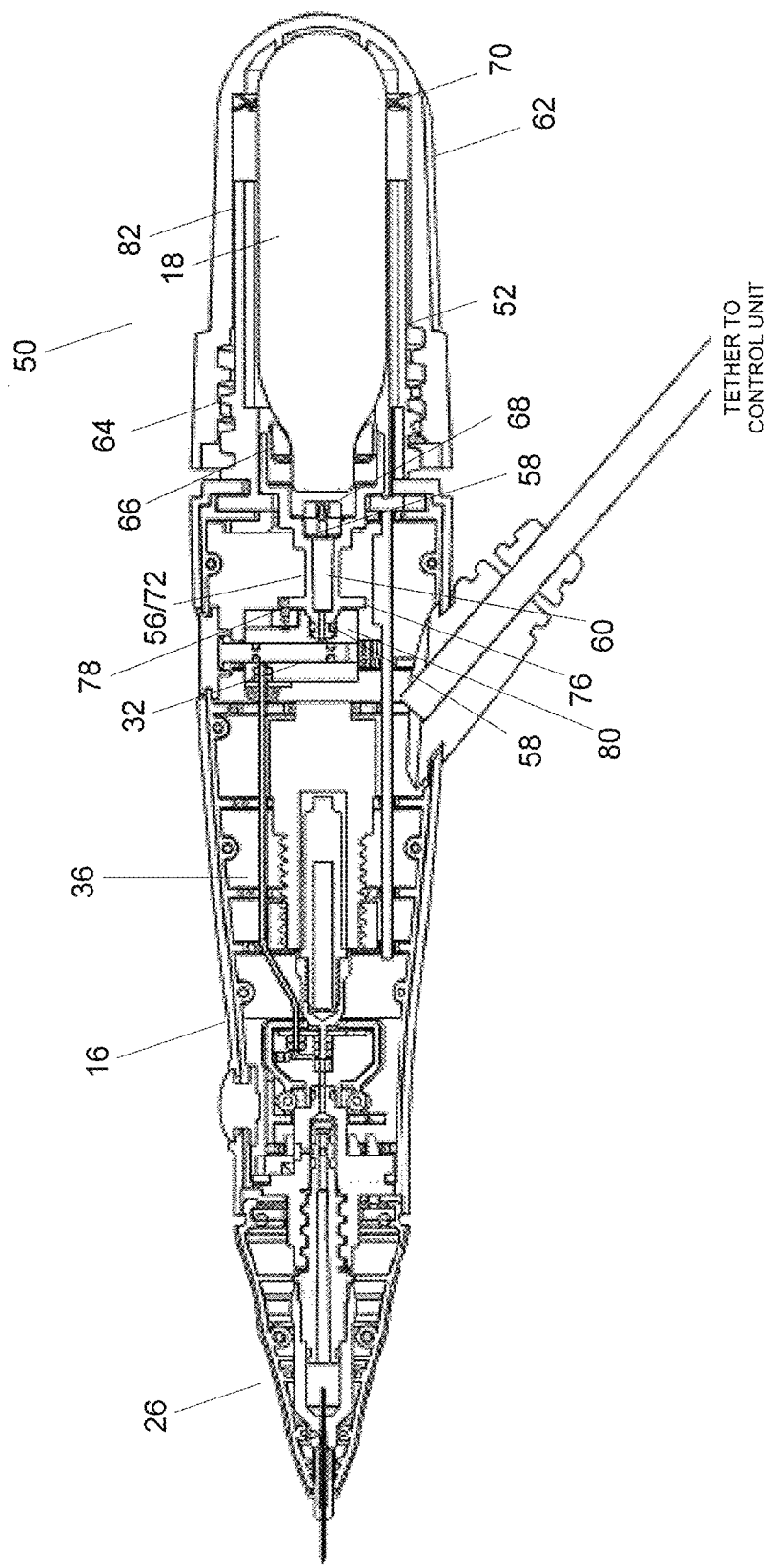
FIG. 2B is a cross-sectional view of the system of FIG. 1A, according to some embodiments of the invention.

FIG. 2B shows a cross-section of the housing 16. This embodiment of the housing 16 may be powered by an external source, hence the attached cable, but could alternatively include a portable power source. As shown, the housing includes a cartridge holder 50. The cartridge holder 50 includes a cartridge receiver 52, which may be configured to hold a pressured refrigerant cartridge 18. The cartridge receiver 52 includes an elongated cylindrical passage 54, which is dimensioned to hold a commercially available cooling fluid cartridge 18. A distal portion of the cartridge receiver 52 includes a filter device 56, which has an elongated conical shape. In some embodiments, the cartridge holder 50 may be largely integrated into the housing 16 as shown, however, in alternative embodiments, the cartridge holder 50 is a wholly separate assembly, which may be pre-provided with a coolant fluid source 18.

The filter device 56 may fluidly couple the coolant fluid source (cartridge) 18 at a proximal end to the valve 32 at a distal end. The filter device 56 may include at least one particulate filter 58. In the shown embodiment, a particulate filter 58 at each proximal and distal end of the filter device 56 may be included. The particulate filter 58 can be configured to prevent particles of a certain size from passing through. For example, the particulate filter 58 can be constructed as a microscreen having a plurality of passages less than 2 microns in width, and thus particles greater than 2 microns would not be able to pass.

The filter device 56 also includes a molecular filter 60 that is configured to capture fluid impurities. In some embodiments, the molecular filter 60 is a plurality of filter media (e.g., pellets, powder, particles) configured to trap molecules of a certain size. For example, the filter media can comprise molecular sieves having pores ranging from 1-20 Å. In another example, the pores have an average size of 5 Å. The molecular filter 60 can have two modalities. In a first mode, the molecular filter 60 will filter fluid impurities received from the cartridge 18. However, in another mode, the molecular filter 60 can capture impurities within the valve 32 and fluid supply tube 36 when the system 10 is not in use, i.e., when the cartridge 18 is not fluidly connected to the valve 32.

Alternatively, the filter device 56 can be constructed primarily from ePTFE (such as a GORE material), sintered polyethylene (such as made by POREX), or metal mesh. The pore size and filter thickness can be optimized to minimize pressure drop while capturing the majority of contaminants. These various materials can be treated to make it hydrophobic (e.g., by a plasma treatment) and/or oleophobic so as to repel water or hydrocarbon contaminants.

It has been found that in some instances fluid impurities may leach out from various aspects of the system 10. These impurities can include trapped moisture in the form of water molecules and chemical gasses. The presence of these impurities is believed to hamper cooling performance of the system 10. The filter device 56 can act as a desiccant that attracts and traps moisture within the system 10, as well as chemicals out gassed from various aspects of the system 10. Alternately the various aspects of the system 10 can be coated or plated with impermeable materials such as a metal.

Figure 2C:
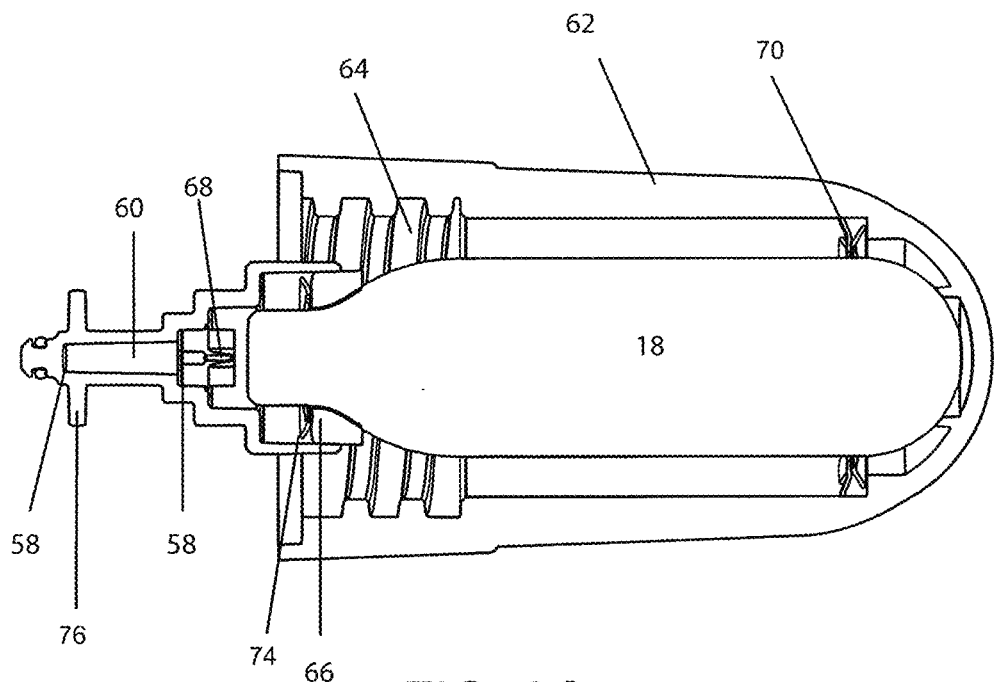
FIGS. 2C and 2D are cross-sectional views showing exemplary operational modes of the system of FIG. 2B.
Figure 2D:
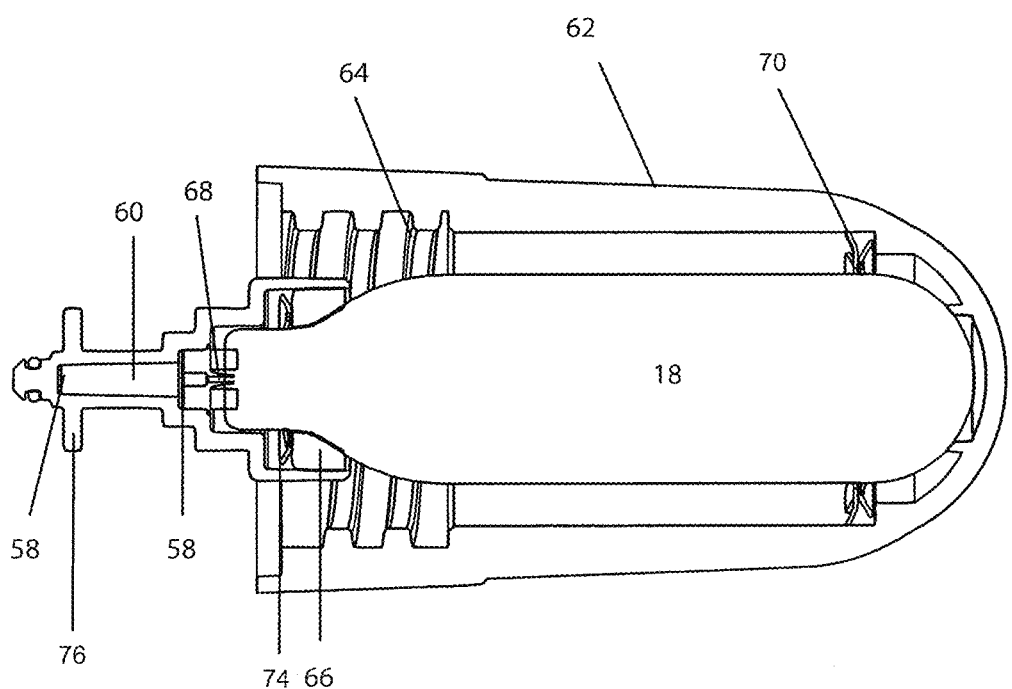

As shown in FIG. 2B and in more detail in FIG. 2C and FIG. 2D, the cartridge 18 can be held by the cartridge receiver 52 such that the cartridge 18 remains intact and unpunctured. In this inactive mode, the cartridge may not be fluidly connected to the valve 32. A removable cartridge cover 62 can be attached to the cartridge receiver 52 such that the inactive mode is maintained while the cartridge is held by the system 10.

In use, the cartridge cover 62 can be removed and supplied with a cartridge containing a cooling fluid. The cartridge cover 62 can then be reattached to the cartridge receiver 52 by turning the cartridge cover 62 until female threads 64 of the cartridge cover 62 engage with male threads of the cartridge receiver 52. The cartridge cover 62 can be turned until resilient force is felt from an elastic seal 66, as shown in FIG. 2C. To place the system 10 into use, the cartridge cover 62 can be further turned until the distal tip of the cartridge 18 is punctured by a puncture pin connector 68, as shown in FIG. 2D. Once the cartridge 18 is punctured, cooling fluid may escape the cartridge by flowing through the filter device 56, where the impurities within the cooling fluid may be captured. The purified cooling fluid then passes to the valve 32, and onto the coolant supply tube 36 to cool the probe 26. In some embodiments the filter device, or portions thereof, may be replaceable.

In some embodiments, the puncture pin connector 68 can have a two-way valve (e.g., ball/seat and spring) that is closed unless connected to the cartridge. Alternately, pressure can be used to open the valve. The valve closes when the cartridge is removed. In some embodiments, there may be a relief valve piloted by a spring which is balanced by high-pressure nitrous when the cartridge is installed and the system is pressurized, but allows the high-pressure cryogen to vent when the cryogen is removed. In addition, the design can include a vent port that vents cold cryogen away from the cartridge port. Cold venting cryogen locally can cause condensation in the form of liquid water to form from the surrounding environment. Liquid water or water vapor entering the system can hamper the cryogenic performance. Further, fluid carrying portions of the cartridge receiver 52 can be treated (e.g., plasma treatment) to become hydrophobic and/or oleophobic so as to repel water or hydrocarbon contaminants.

Figure 3A:
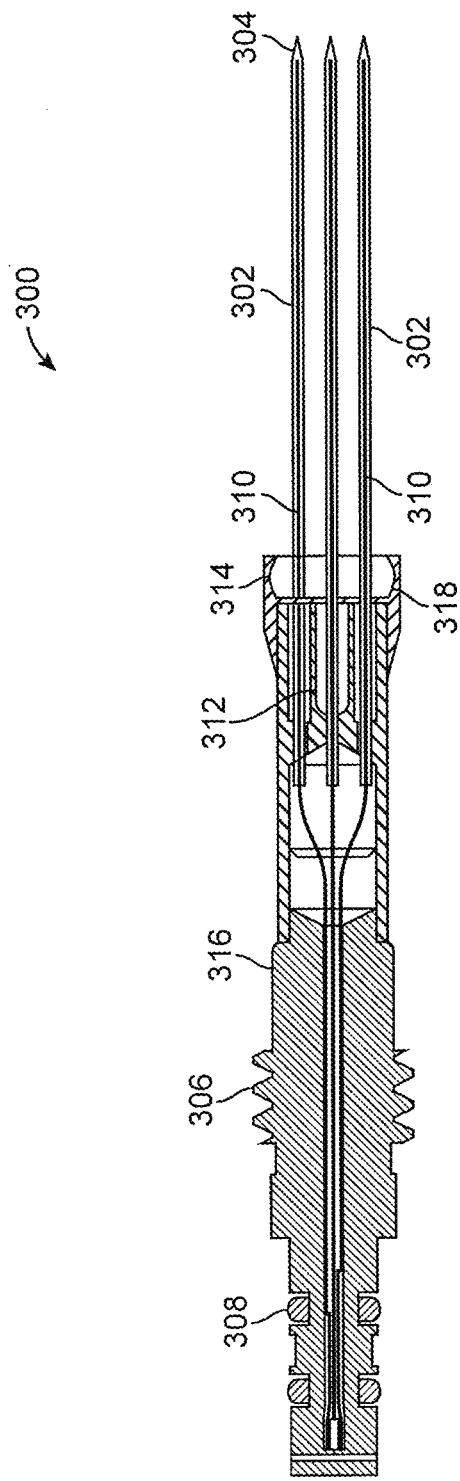
FIGS. 3A-3D illustrate exemplary embodiment of a needle probe, according to some embodiments of the invention.
Figure 3B:
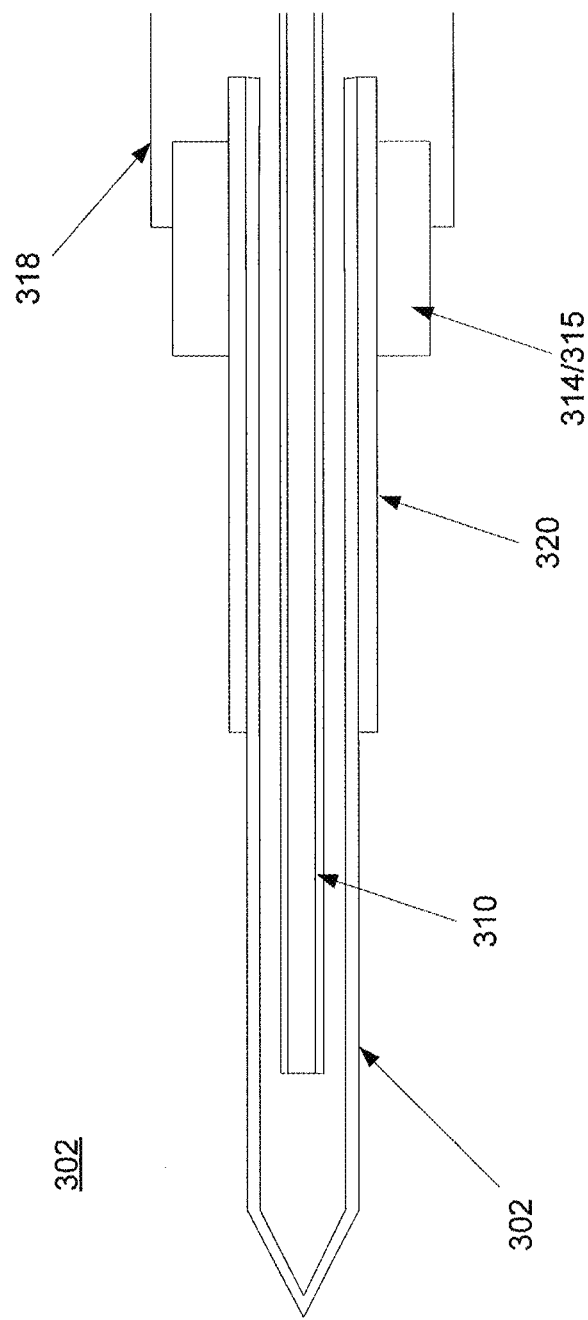

Turning now to FIG. 3A and FIG. 3B, an exemplary embodiment of probe 300 having multiple needles 302 is described. In FIG. 3A, probe housing 316 includes threads 306 that allow the probe to be threadably engaged with the housing 16 of a cryogenic device. O-rings 308 fluidly seal the probe housing 316 with the device housing 16 and prevent coolant from leaking around the interface between the two components. Probe 300 includes an array of three distally extending needle shafts 302, each having a sharpened, tissue penetrating tip 304. Using three linearly arranged needles allows a greater area of tissue to be treated as compared with a single needle. In use, coolant flows through lumens 310 into the needle shafts 302 thereby cooling the needle shafts 302. Ideally, only the distal portion of the needle shaft 302 would be cooled so that only the target tissue receives the cryogenic treatment. However, as the cooling fluid flows through the probe 300, probe temperature decreases proximally along the length of the needle shafts 302 towards the probe hub 318. The proximal portion of needle shaft 302 and the probe hub 318 contact skin and may become very cold (e.g. −20° C. to −25° C.) and this can damage the skin in the form of blistering or loss of skin pigmentation. Therefore it would be desirable to ensure that the proximal portion of needle shaft 302 and hub 318 remains warmer than the distal portion of needle shaft 302. A proposed solution to this challenge is to include a heater element 314 that can heat the proximal portion of needle shaft 302 and an optional temperature sensor 312 to monitor temperature in this region. To further this, a proximal portion of the needle shaft 302 can be coated with a highly thermally conductive material, e.g., gold, that is conductively coupled to both the needle shaft 302 and heater element 314. Details of this construction are disclosed below.

In the exemplary embodiment of FIG. 3A, resistive heater element 314 is disposed near the needle hub 318 and near a proximal region of needle shaft 302. The resistance of the heater element is preferably 1Ω to 1 KΩ, and more preferably from 5Ω to 50Ω. Additionally, a temperature sensor 312 such as a thermistor or thermocouple is also disposed in the same vicinity. Thus, during a treatment as the needles cool down, the heater 314 may be turned on in order to heat the hub 318 and proximal region of needle shaft 302, thereby preventing this portion of the device from cooling down as much as the remainder of the needle shaft 302. The temperature sensor 312 may provide feedback to controller 22 and a feedback loop can be used to control the heater 314. The cooling power of the nitrous oxide may eventually overcome the effects of the heater, therefore the microprocessor may also be programmed with a warning light and/or an automatic shutoff time to stop the cooling treatment before skin damage occurs. An added benefit of using such a heater element is the fact that the heat helps to moderate the flow of cooling fluid into the needle shaft 302 helping to provide more uniform coolant mass flow to the needles shaft 302 with more uniform cooling resulting.

The embodiment of FIG. 3A illustrates a heater fixed to the probe hub. In other embodiments, the heater may float, thereby ensuring proper skin contact and proper heat transfer to the skin. Examples of floating heaters are disclosed in commonly assigned Int'l Pub. No. WO 2010/075448 entitled "Skin Protection for Subdermal Cryogenic Remodeling for Cosmetic and Other Treatments," the entirety of which is incorporated by reference herein.

In this exemplary embodiment, three needles are illustrated. One of skill in the art will appreciate that a single needle may be used, as well as two, four, five, six, or more needles may be used. When a plurality of needles are used, they may be arranged in any number of patterns. For example, a single linear array may be used, or a two dimensional or three dimensional array may be used. Examples of two dimensional arrays include any number of rows and columns of needles (e.g. a rectangular array, a square array, elliptical, circular, triangular, etc.), and examples of three dimensional arrays include those where the needle tips are at different distances from the probe hub, such as in an inverted pyramid shape.

FIG. 3B illustrates a cross-section of the needle shaft 302 of needle probe 300. The needle shaft can be conductively coupled (e.g., welded, conductively bonded, press fit) to a conductive heater 314 to enable heat transfer therebetween. The needle shaft 302 is generally a small (e.g., 20-30 gauge) closed tip hollow needle, which can be between about 0.2 mm and 15 cm, preferably having a length from about 0.3 cm to about 1.5 cm. The conductive heater element 314 can be housed within a conductive block 315 of high thermally conductive material, such as aluminum and include an electrically insulated coating, such as Type III anodized coating to electrically insulate it without diminishing its heat transfer properties. The conductive block 315 can be heated by a resister or other heating element (e.g. cartridge heater, nichrome wire, etc.) bonded thereto with a heat conductive adhesive, such as epoxy. A thermistor can be coupled to the conductive block 315 with heat conductive epoxy allows temperature monitoring. Other temperature sensors may also be used, such as a thermocouple.

A cladding 320 of conductive material is directly conductively coupled to the proximal portion of the shaft of the needle 302, which can be stainless steel. In some embodiments, the cladding 320 is a layer of gold, or alloys thereof, coated on the exterior of the proximal portion of the needle shaft 302. In some embodiments, the exposed length of cladding 320 on the proximal portion of the needle is 2-100 mm. In some embodiments, the cladding 320 can be of a thickness such that the clad portion has a diameter ranging from 0.017-0.020 in., and in some embodiments 0.0182 in. Accordingly, the cladding 320 can be conductively coupled to the material of the needle 302, which can be less conductive, than the cladding 320. The cladding 320 may modify the lateral force required to deflect or bend the needle 26. Cladding 320 may be used to provide a stiffer needle shaft along the proximal end in order to more easily transfer force to the leading tip during placement and allow the distal portion of the needle to deflect more easily when it is dissecting a tissue interface within the body. The stiffness of needle 26 can vary from one end to the other end by other means such as material selection, metal tempering, variation of the inner diameter of the needle 26, or segments of needle shaft joined together end-to-end to form one contiguous needle 26. In some embodiments, increasing the stiffness of the distal portion of the needle 26 can be used to flex the proximal portion of the needle to access difficult treatment sites as in the case of upper limb spasticity where bending of the needle outside the body may be used to access a target peripheral nerve along the desired tissue plane.

In some embodiments, the cladding 320 can include sub-coatings (e.g., nickel) that promote adhesion of an outer coating that would otherwise not bond well to the needle shaft 302. Other highly conductive materials can be used as well, such as copper, silver, aluminum, and alloys thereof. In some embodiments, a protective polymer or metal coating can cover the cladding to promote biocompatibility of an otherwise non-biocompatible but highly conductive cladding material. Such a biocompatible coating however, would be applied to not disrupt conductivity between the conductive block 315. In some embodiments, an insulating layer, such as a ceramic material, is coated over the cladding 320, which remains conductively coupled to the needle shaft 302.

Figure 3C:
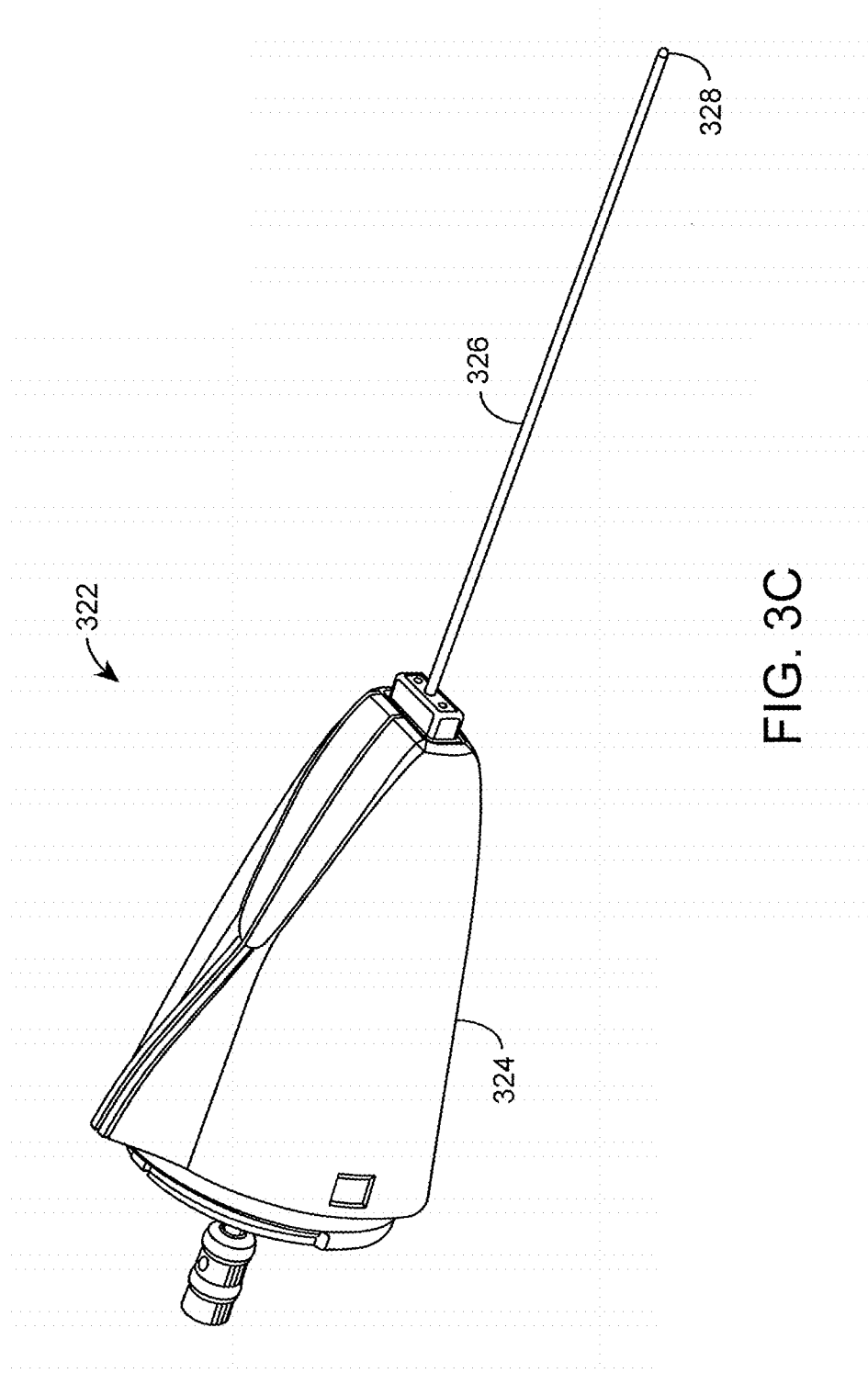
Figure 3D:
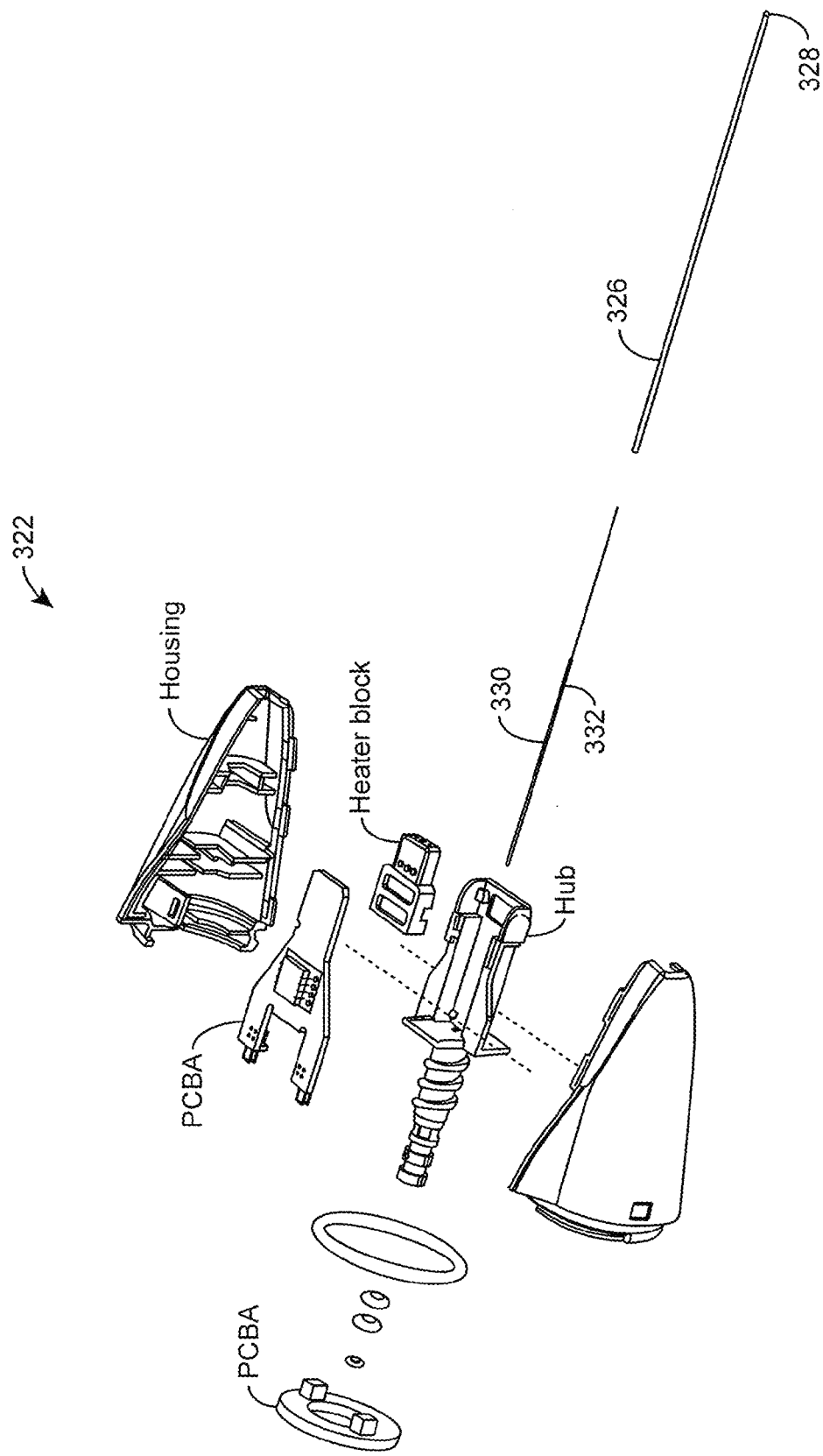

FIGS. 3C and 3D illustrates a detachable probe tip 322 having a hub connector 324 and an elongated probe 326. The probe tip 322 shares much of its construction with probe 300. However, the elongated probe 326 features a blunt tip 328 that is adapted for blunt dissection of tissue. The blunt tip 328 can feature a full radius tip, less than a full radius tip, or conical tip. In some embodiments, a dulled or truncated needle is used. The elongated probe 326 can be greater than 20 gauge in size, and in some embodiments range in size from 25-30 gauge. As with the embodiments described above, an internal supply tube 330 extends in cantilever. However, the exit of the supply tube 330 can be disposed at positions within the elongated probe 326 other than proximate the blunt tip 328. Further, the supply tube 330 can be adapted to create an elongated zone of cooling, e.g., by having multiple exit points for cryofluid to exit from.

The elongated probe 326 and supply tube 330 may be configured to resiliently bend in use, throughout their length at angles approaching 120°, with a 5-10 mm bend radius. This may be very challenging considering the small sizes of the elongated probe 326 and supply tube 330, and also considering that the supply tube 330 is often constructed from fused silica. Accordingly, the elongated probe 326 can be constructed from a resilient material, such as stainless steel, and of a particular diameter and wall thickness [0.004 to 1.0 mm], such that the elongated probe in combination with the supply tube 330 is not overly resilient so as to overtly resist manipulation, but sufficiently strong so as to prevent kinking that can result in coolant escaping. For example, the elongated probe can be 15 gauge or smaller in diameter, even ranging from 20-30 gauge in diameter. The elongated probe can have a very disparate length to diameter ratio, for example, the elongated probe can be greater than 30 mm in length, and in some cases range from 30-100 mm in length. To further the aforementioned goals, the supply tube 330 can include a polymer coating 332, such as a polyimide coating that terminates approximately halfway down its length, to resist kinking and aid in resiliency. The polymer coating 332 can be a secondary coating over a primary polyimide coating that extends fully along the supply tube. However, it should be understood that the coating is not limited to polyimide, and other suitable materials can be used. In some embodiments, the flexibility of the elongated probe 326 will vary from the proximal end to the distal end. For example, by creating certain portions that have more or less flexibility than others. This may be done, for example, by modifying wall thickness, adding material (such as the cladding discussed above), and/or heat treating certain portions of the elongated probe 326 and/or supply tube 330. For example, decreasing the flexibility of elongated probe 326 along the proximal end can improve the transfer of force from the hand piece to the elongated probe end for better feel and easier tip placement for treatment. The elongated probe and supply line 330 are may be configured to resiliently bend in use to different degrees along the length at angles approaching 120°, with a varying bend radius as small as 5 mm. In some embodiments, the elongated probe 326 will have external markings along the needle shaft indicating the length of needle inserted into the tissue.

Figure 4A:
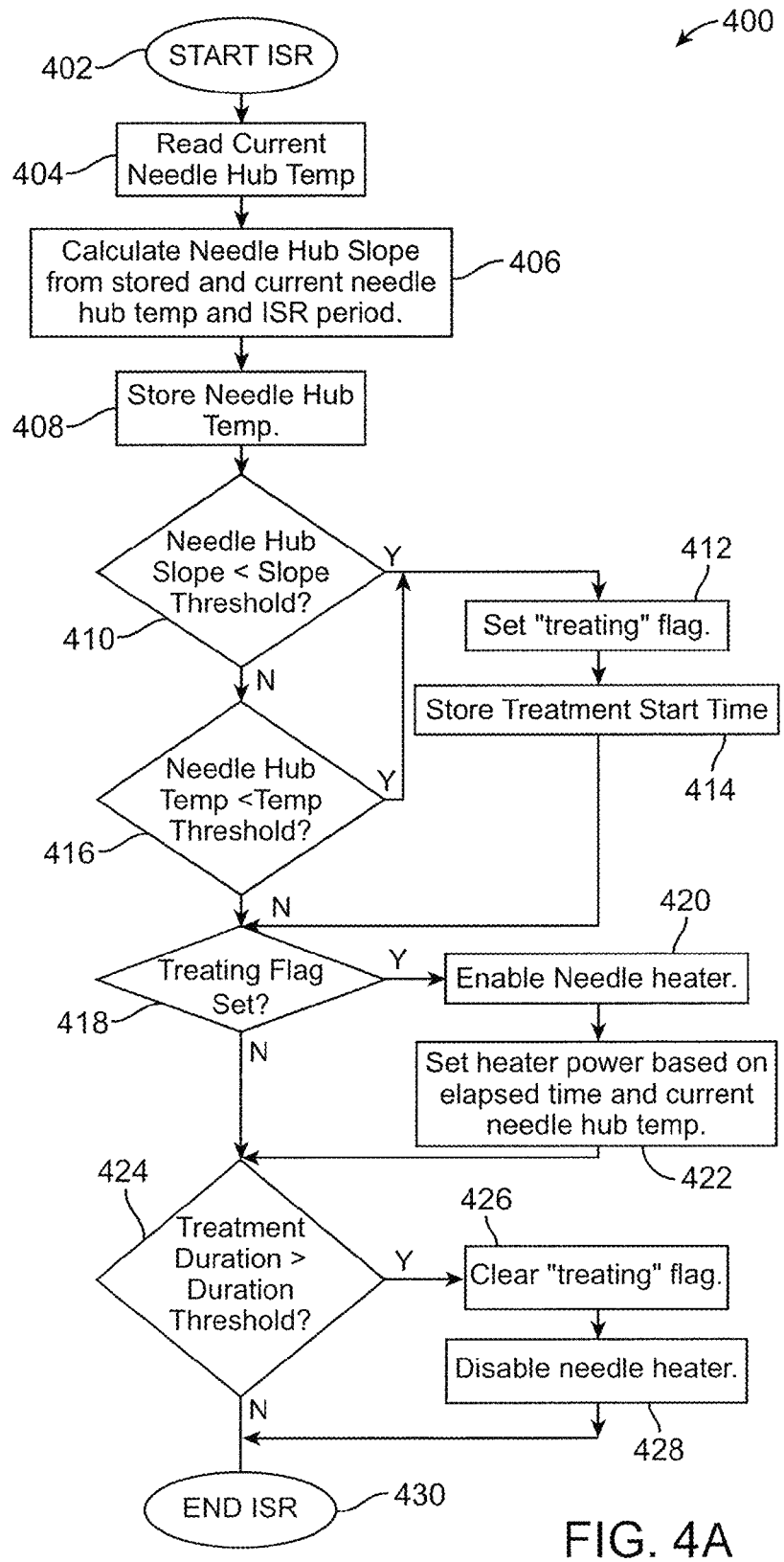
FIG. 4A is a flow chart illustrating an exemplary algorithm for heating the needle probe of FIG. 3A, according to some embodiment of the invention.

An exemplary algorithm 400 for controlling the heater element 314, and thus for transferring heat to the cladding 320, is illustrated in FIG. 4A. In FIG. 4A, the start of the interrupt service routine (ISR) 402 begins with reading the current needle hub temperature 404 using a temperature sensor such as a thermistor or thermocouple disposed near the needle hub. The time of the measurement is also recorded. This data is fed back to controller 22 where the slope of a line connecting two points is calculated. The first point in the line is defined by the current needle hub temperature and time of its measurement and the second point consists of a previous needle hub temperature measurement and its time of measurement. Once the slope of the needle hub temperature curve has been calculated 406, it is also stored 408 along with the time and temperature data. The needle hub temperature slope is then compared with a slope threshold value 410. If the needle hub temperature slope is less than the threshold value then a treating flag is activated 412 and the treatment start time is noted and stored 414. If the needle hub slope is greater than or equal to the slope threshold value 410, an optional secondary check 416 may be used to verify that cooling has not been initiated. In step 416, absolute needle hub temperature is compared to a temperature threshold. If the hub temperature is less than the temperature threshold, then the treating flag is activated 412 and the treatment start time is recorded 414 as previously described. As an alternative, the shape of the slope could be compared to a norm, and an error flag could be activated for an out of norm condition. Such a condition could indicate the system was not heating or cooling sufficiently. The error flag could trigger an automatic stop to the treatment with an error indicator light. Identifying the potential error condition and possibly stopping the treatment may prevent damage to the proximal tissue in the form of too much heat, or too much cooling to the tissue. The algorithm preferably uses the slope comparison as the trigger to activate the treatment flag because it is more sensitive to cooling conditions when the cryogenic device is being used rather than simply measuring absolute temperature. For example, a needle probe exposed to a cold environment would gradually cool the needle down and this could trigger the heater to turn on even though no cryogenic cooling treatment was being conducted. The slope more accurately captures rapid decreases in needle temperature as are typically seen during cryogenic treatments.

When the treatment flag is activated 418 the needle heater is enabled 420 and heater power may be adjusted based on the elapsed treatment time and current needle hub temperature 422. Thus, if more heat is required, power is increased and if less heat is required, power is decreased. Whether the treatment flag is activated or not, as an additional safety mechanism, treatment duration may be used to control the heater element 424. As mentioned above, eventually, cryogenic cooling of the needle will overcome the effects of the heater element. In that case, it would be desirable to discontinue the cooling treatment so that the proximal region of the probe does not become too cold and cause skin damage. Therefore, treatment duration is compared to a duration threshold value in step 424. If treatment duration exceeds the duration threshold then the treatment flag is cleared or deactivated 426 and the needle heater is deactivated 428. If the duration has not exceeded the duration threshold 424 then the interrupt service routine ends 430. The algorithm then begins again from the start step 402. This process continues as long as the cryogenic device is turned on.

Preferred ranges for the slope threshold value may range from about −5° C. per second to about −90° C. per second and more preferably range from about −30° C. per second to about −57° C. per second. Preferred ranges for the temperature threshold value may range from about 15° C. to about 0° C., and more preferably may range from about 0° C. to about 10° C. Treatment duration threshold may range from about 15 seconds to about 75 seconds.

It should be appreciated that the specific steps illustrated in FIG. 4A provide a particular method of heating a cryogenic probe, according to an embodiment of the present invention. Other sequences of steps may also be performed according to alternative embodiments. For example, alternative embodiments of the present invention may perform the steps outlined above in a different order. Moreover, the individual steps illustrated in FIG. 13 may include multiple sub-steps that may be performed in various sequences as appropriate to the individual step. Furthermore, additional steps may be added or removed depending on the particular applications.

Figure 4B:
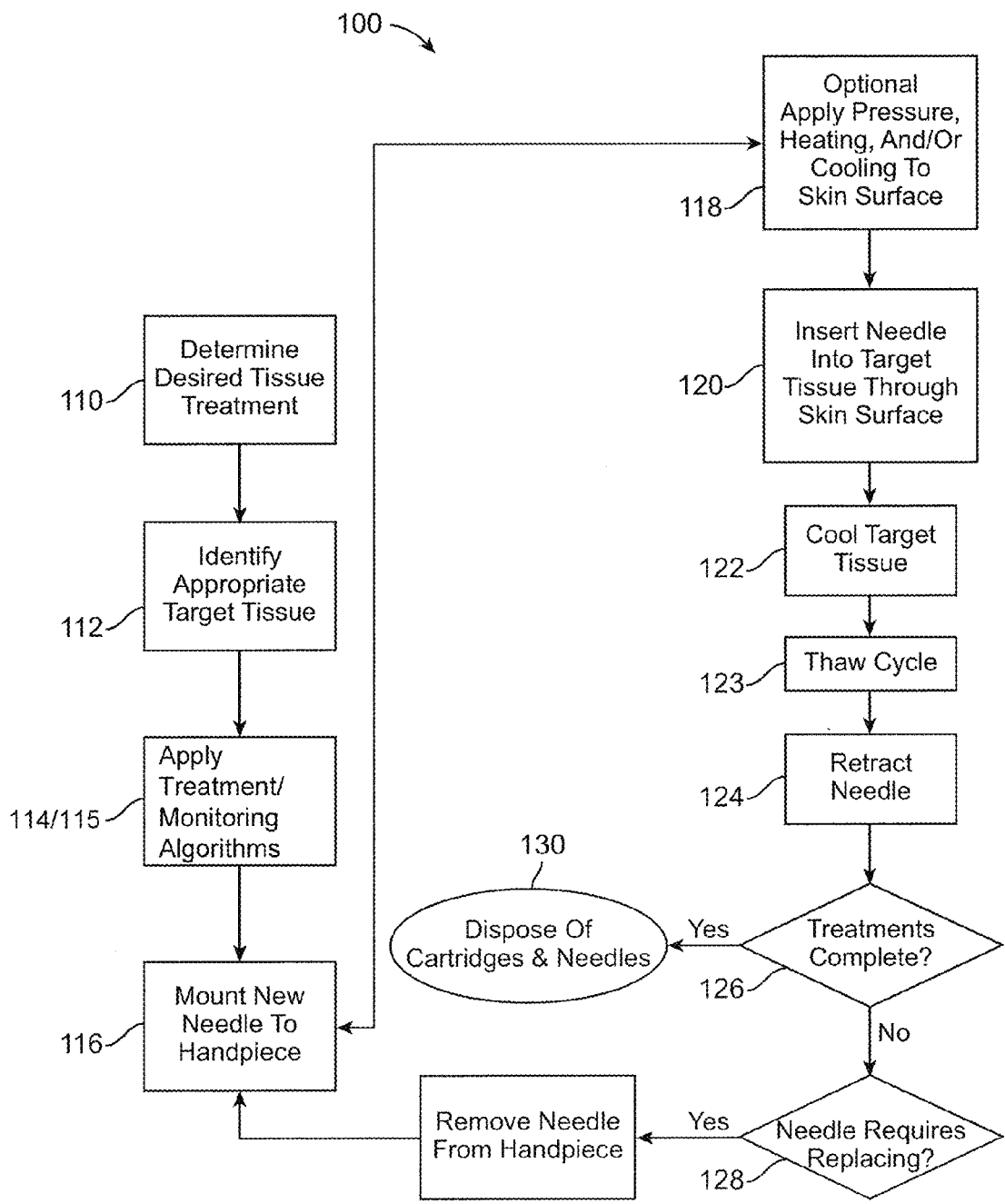
FIG. 4B is a flow chart schematically illustrating an exemplary method for treatment using the disposable cryogenic probe and system of FIGS. 1A and 1B, according to some embodiments of the invention.

The heating algorithm may be combined with a method for treating a patient. Referring now to FIG. 4B, a method 100 facilitates treating a patient using a cryogenic cooling system having a reusable or disposable handpiece either of which that can be self-contained or externally powered with replaceable needles such as those of FIG. 1B and a limited capacity battery or metered electrical supply. Method 100 generally begins with a determination 110 of the desired tissue therapy and results, such as the inhibition of pain from a particular site. Appropriate target tissues for treatment are identified 112 (a tissue that transmits the pain signal), allowing a target treatment depth, target treatment temperature profile, or the like to be determined. Step 112 may include performing a tissue characterization and/or device diagnostic algorithm, based on power draw of system 10, for example.

The application of the treatment algorithm 114 may include the control of multiple parameters such as temperature, time, cycling, pulsing, and ramp rates for cooling or thawing of treatment areas. In parallel with the treatment algorithm 114, one or more power monitoring algorithms 115 can be implemented. An appropriate needle assembly can then be mounted 116 to the handpiece, with the needle assembly optionally having a needle length, skin surface cooling chamber, needle array, and/or other components suitable for treatment of the target tissues. Simpler systems may include only a single needle type, and/or a first needle assembly mounted to the handpiece.

Pressure, heating, cooling, or combinations thereof may be applied 118 to the skin surface adjacent the needle insertion site before, during, and/or after insertion 120 and cryogenic cooling 122 of the needle and associated target tissue. Non-target tissue directly above the target tissue can be protected by directly conducting energy in the form of heat to the cladding on a proximal portion of the needle shaft during cooling. Upon completion of the cryogenic cooling phase the needles will need additional "thaw" time 123 to thaw from the internally created cooling zone to allow for safe removal of the probe without physical disruption of the target tissues, which may include, but not be limited to nerves, muscles, blood vessels, or connective tissues. This thaw time can either be timed with the refrigerant valve shut-off for as short a time as possible, preferably under 15 seconds, more preferably under 5 seconds, manually or programmed into the controller to automatically shut-off the valve and then pause for a chosen time interval until there is an audible or visual notification of treatment completion.

Heating of the needle may be used to prevent unwanted skin damage using the apparatus and methods previously described. The needle can then be retracted 124 from the target tissue. If the treatment is not complete 126 and the needle is not yet dull 128, pressure and/or cooling can be applied to the next needle insertion location site 118, and the additional target tissue treated. However, as small gauge needles may dull after being inserted only a few times into the skin, any needles that are dulled (or otherwise determined to be sufficiently used to warrant replacement, regardless of whether it is after a single insertion, 5 insertions, or the like) during the treatment may be replaced with a new needle 116 before the next application of pressure/cooling 118, needle insertion 120, and/or the like. Once the target tissues have been completely treated, or once the cooling supply canister included in the self-contained handpiece is depleted, the used canister and/or needles can be disposed of 130. The handpiece may optionally be discarded.

2. METHODS FOR TREATING SPASTICITY

Methods can be implemented using one or more aspects of the system disclosed above for treatment of spasticity. Generally, at least one needle of a needle probe is placed proximate to a motor nerve that is in communication with a skeletal muscle afflicted with spasticity. The needle probe can include more needles, however only one is required. A treatment algorithm is then enacted to provide the needle with cooling fluid for a predetermined amount of time. Further, warming phases may take place before and after the cooling fluid is provided, however, the warming phases are not required for efficacy of treatment.

The treatment algorithm is configured to provide coolant long enough to remodel tissue of the motor nerve and thereby mitigate spasticity of the afflicted skeletal muscle. However, the coolant is not provided for an excessive period of time or at too low of a temperature, since control of the skeletal muscle is desired. Similar prior systems provided similar effect to facial muscles; however, this was to mitigate wrinkles, and not to mitigate spasticity. For the former, the desired result was to more or less eliminate both reflexive and intentional control of certain wrinkle-inducing facial muscles to achieve a BOTOX-like effect. However, here that would not be desirable since muscles affected with spasticity are often limb muscles that are needed to perform everyday living functions for the affected patient. With spasticity, there is usually an imbalance of activity, such that there is a stronger pull in one direction, such as into elbow flexion. Accordingly, treatment of spasticity using the systems disclosed herein include providing a treatment algorithm such that balance of activity is normalized.

Hence, care must be taken to avoid excessive treatment of the motor nerve, while still providing enough treatment to mitigate spasticity. Accordingly, in some cases treatment can result in a complete elimination of spasticity, at least for a certain period of time (e.g., weeks), or a limited amount of spasticity may be present after treatment. In the latter case, the spasticity is mitigated to improve quality of life.

Spastic movement disorders also typically feature a loss of stabilization of an affected limb or the head from the trunk, so a thorough assessment requires this to be analyzed as well. Accordingly, treatment of spasticity using the systems disclosed herein include providing a treatment algorithm such that muscle stabilization is normalized or can be made more easily normalized by post-treatment physical therapy.

Additional effects of spasticity are likely to impact on assessment of spastic muscles. If a muscle has impaired function following an upper motor neuron lesion, other changes such as increased muscle stiffness are likely to affect the feeling of resistance to passive stretch. Accordingly, treatment of spasticity using the systems disclosed herein include providing a treatment algorithm such that muscle stiffness caused by spasticity is mitigated.

Needle probes for treating spasticity configured to access relatively deep locations within tissue to treat deeper nerves require longer needles. Longer needles of a multi-needle needle probe may also require a smaller gauge (larger diameter) so that each needles has sufficient rigidity to maintain consistent spacing when placed deep in the tissue, but not so large as to create significant mechanical injury to the skin and tissue when inserted (e.g. larger than 20 ga). Alternate configurations of the needle prove have 2 or more needles spaced generally 3-7 mm apart of lengths ranging up to 20 mm or greater, typically of 25 gauge to 23 gauge. Single needle configurations can be even longer and may require active nerve location such as ultrasound or electrical nerve stimulation to guide placement of the needle. The long, single needle does not require the skin protection elements of the (e.g. active heating of the skin warmer and/or cladding) found in the shorter needle as the cryozone can be placed sufficiently deep below the dermis to prevent injury.

Devices used for the spasticity study described below were configured with 3 needles each of 27 gauge, 6 mm length, and 2 mm spacing between needles. Although this configuration was effective, it is believe that a different design may be more effective and/or be easier to use. During the treatment of upper limb spasticity, nerves were imaged with ultrasounds and found to range in size often up to diameters of 5 mm. This made it difficult or impossible to place the nerve between needles with 2 mm spacing. Hence, a needle probe may include needles placed 5-8 mm apart and 12 mm in length or greater, which would more effectively treat larger nerves such as those targeted for upper limb spasticity. With increased spacing, system modifications may be required to increase cooling power to ensure that the target temperature is reached between adjacent needles to achieve creation of a preferred cooling zone volume, also referred to herein as a cryozone. For example, in some embodiments, devices and treatment phases may be configured to generate cryozones (defined by a 0 degree isotherm) having a cross-sectional area of approximately 14-55 $mm^2$ (e.g., 27 $mm^2$). Optionally, the devices and treatment phases may be configured to generate cryozones having a volume of approximately 65-125 $mm^3$ (e.g., 85 $mm^3$). This could be done by increasing the flow rate of the cryogen or by changing to a cryogen with more cooling power. Power to the heater can also be decreased, minimized, or eliminated, since the location is not generally associated with aesthetics, thus, allowing wider spacing between needles.

Variability from patient to patient in the depth of the target nerve created challenges with early treatments. Using PENS to determine the approximate location and depth of the nerve and then by placing a 12 mm needle probe to that approximate location and depth, either by partially inserting it or by compressing the tissue (by pressing hard), the PENS guided treatments were generally more successful.

A single needle probe configuration (e.g. 1×90 mm) can also be used, optionally with the help of ultrasound nerve location or percutaneous electrical nerve stimulation (PENS) to place the single needle adjacent to one side of the nerve. This configuration would be helpful for treating nerves that are very deep, i.e., greater than 15 mm below the dermis. Larger nerves may associated with spasticity may require treatment from both sides to make sure that the cold zone created by the needle fully covers the nerve. Adjacent treatments placing a needle to either side of the nerve during two successive treatment phases will still provide an effective treatment of the entire nerve cross-section.

3. UPPER LIMB SPASTICITY TREATMENT STUDY

This was a prospective, non-randomized, unblinded multi-center study for treatment of upper limb spasticity.

3.1 Purpose of the Study

The purpose of the study was to evaluate the temporary relief of pain and symptoms in the upper arm in Subjects with upper limb spasticity secondary to stroke, cerebral palsy, multiple sclerosis, traumatic brain injury, or similar disorder. Subjects were prospectively enrolled to treat upper limb spasticity. Subjects received a unilateral treatment. All Subjects completed a minimum follow-up period of 56 days.

3.2 Study Endpoionts

The primary endpoint of the study was:
A decrease in pain and symptoms caused by hypertonia of the upper arm as measured by an improvement of 1 point or greater on the Modified Ashworth Scale at Day 7.

The Secondary endpoints of the study were:
Improvement in spasticity as measured by the Tardieu Scale.
Improvement in spasm frequency and intensity as measured by the Penn Spasm Score.
Improvement in upper extremity motor recovery as measured by the Fugl-Meyer Scale (post stroke Subjects only).
Subject assessed change in Mean Spasticity Numerical Rating Scale (NRS) score.
Improvement in pain as assess by visual analog scale (VAS).
Duration of treatment effect.
Additional assessments include the following questions:
Would Subject recommend treatment to a family member?
Would Subject have treatment again if available?
Safety measures were:
Adverse events and SAEs/UADEs will be assessed at all visits. Incidence of serious adverse events (SAEs) and unanticipated adverse device effects (UADEs) will be recorded.

3.3 Assessement Ratings

The Modified Ashworth Scale (MAS) is 6-point scale designed to assess muscle tone and spasticity through the flexion or extension of a joint. Muscle response is graded on a scale from 0 (no increase in muscle tone) to 4 (affected parts rigid in flexion or extension). This includes a 1+ rating, which further distinguishes the types of increase in muscle tone from those described by a 1 or 2 rating. See Bohannon, R. and Smith, M. (1987), Interrater reliability of a modified Ashworth scale of muscle spasticity. Physical Therapy, 67(2): 206. MAS was assessed at the following time points: pre-procedure, immediately post-treatment, Day 7 and Day 30.

The Tardieu Scale uses the application of stretch at several velocities to quantify muscle response and assess muscle spasticity. See Boyd, R. N. and Graham, H. K. (1999), Objective measurement of clinical findings in the use of botulinum toxin type A for the management of children with cerebral palsy. European Journal of Neurology, 6: s23-s35. It involves the use of three specified velocities (V1, V2 and V3). For each stretch, quality of muscle reaction (X) is recorded on a 6-point scale from 0 (no resistance throughout passive movement) to 5 (immovable joint). The angle of muscle reaction (Y) is assessed, as well as the angle of catch (R1) and the full range of motion (R2). The spasticity angle can be calculated from the R1 and R2 assessments, where a large difference indicates a greater dynamic component and a small difference indicates predominantly fixed contracture. The Tardieu Scale was assessed at the following time points: pre-procedure, immediately post-treatment, Day 7 and Day 30.

The Penn Spasm Score, which is a patient reported score, consists of two sub-scales: the spasm frequency score and the spasm severity scale. See Penn R D, Savoy S M, Corcos D, Latash M, Gottlieb G, Parke B, Kroin J S. Intrathecal baclofen for severe spinal spasticity. N Engl J Med. 1989 Jun. 8; 320(23):1517-21. The Penn spasm frequency is assessed on a 5-point scale from 0 (no spasms) to 4 (spasms occurring more than ten times per hour). The spasm severity scale consists of three ratings, which are 1 (mild), 2 (moderate) and 3 (severe). The Penn Spasm Score was assessed at the following time points: pre-procedure, immediately post-treatment, Day 7 and Day 30.

The Fugl-Meyer Scale is an assessment consisting of 38 movements, each rated by the investigator as "0" (cannot perform), "1" (can partially perform) or "2" (can perform fully). The scale was designed for measuring motor and sensory impairment in post-stroke patients. See Sullivan, K et al. Fugl-Meyer assessment of sensorimotor function after stroke: Standardized training procedure for clinical practice and clinical trials. Stroke. 2011; 42:427-432. The Fugl-Meyer Scale is assessed only in patients who have had a stroke. It was assessed at the following time points: pre-procedure, immediately post-treatment, Day 7 and Day 30.

The Mean Spasticity Rating Scale (NRS) score was assessed by asking subjects "On a scale of '0 to 10' please indicate the average level of your spasticity over the last 24 hours" where "0" equals no spasticity and "10" equals the worst possible spasticity. "No spasticity" was defined as the time prior to the onset of their spasticity. The Mean Spasticity Rating Scale score was collected at the following time points: pre-procedure, immediately post-treatment, Day 7 and Day 30.

The Visual Analog Scale (VAS) is a 0 to 10 scale in which subjects rated pain, where zero equals no pain and 10 equals very severe pain. VAS was collected at the following time points: pre-procedure, immediately post-treatment, Day 7 and Day 30.

Duration of treatment effect was assessed at Day 7, Day 30, and Day 56. At Day 7 and Day 30, duration of treatment effect was assessed by the Investigator. At Day 56 and beyond, Subjects were asked if they were having an effect from the treatment via phone call follow-up.

Subjects completed the additional assessment questions at Day 7, Day 30 and Day 56. These questions are described in Section 5.2 along with the results.

3.4 Subject Selection

Inclusion criteria included:
1. Male or female, 18 years of age and older.
2. Trial participants must have a confirmed diagnosis that results in spasticity involving muscle innervated by the musculocutaneous nerve (MCN).
3. Any medications must be maintained on a stable schedule for at least two weeks prior to treatment. No washout period is allowed.
4. Must have an average score on the Modified Ashworth Scale for Spasticity of ≥2 over the last 30 days in the elbow.
5. Subject, in the Investigator's opinion, will not be exposed to unacceptable risk by participation.

Exclusion criteria included:
1. Previous surgical intervention that altered the target neural anatomy of the upper limb.
2. Any injection (neurolytic, sclerosing, anesthetic, etc.) to the upper limb within the last 4 months.
3. Current enrollment in an investigational drug or device study that specifically targets spasticity management.
4. Allergy or intolerance to local anesthesia.
5. Any local skin condition at the treatment site that in the investigator's opinion would adversely affect treatment or outcomes
6. Any chronic medication use (prescription, over-the-counter, etc.) that in the investigator's opinion would affect study participation or subject safety.
7. Diagnosis of cryoglobulinemia, paroxysmal cold hemoglobinuria, cold urticaria, Raynaud's disease, open and/or infected wounds.
8. Diagnosis of progressive neurologic diseases such as ALS.
9. For any reason, in the opinion of the investigator, the subject may not be a suitable candidate for study participation (i.e., history of noncompliance, drug dependency, any related upper limb injury, etc.).

3.5 Study Treatment

Figure 5:
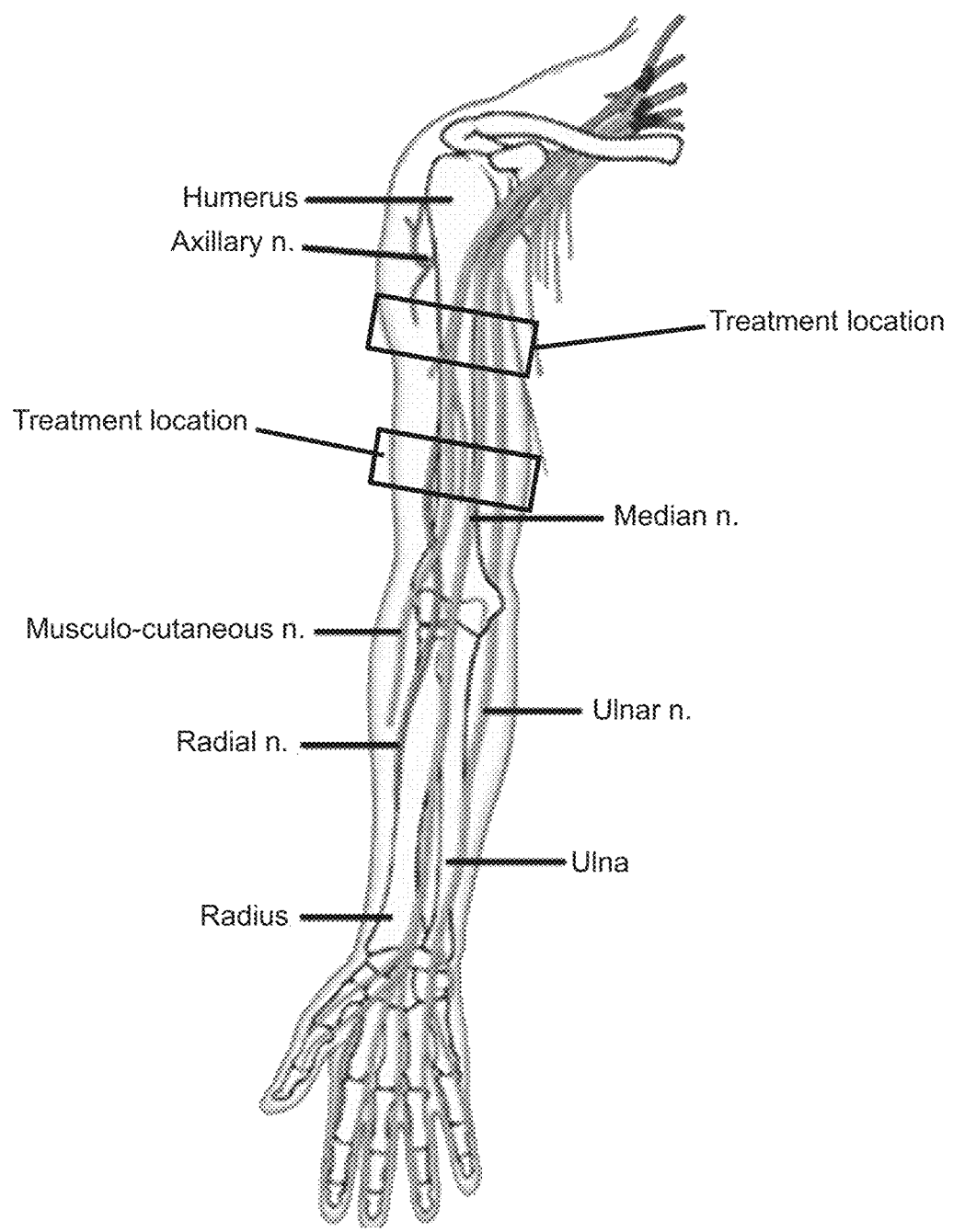
FIG. 5 shows an anatomical diagram showing treatment locations, according to some embodiments of the invention.
Figure 6:
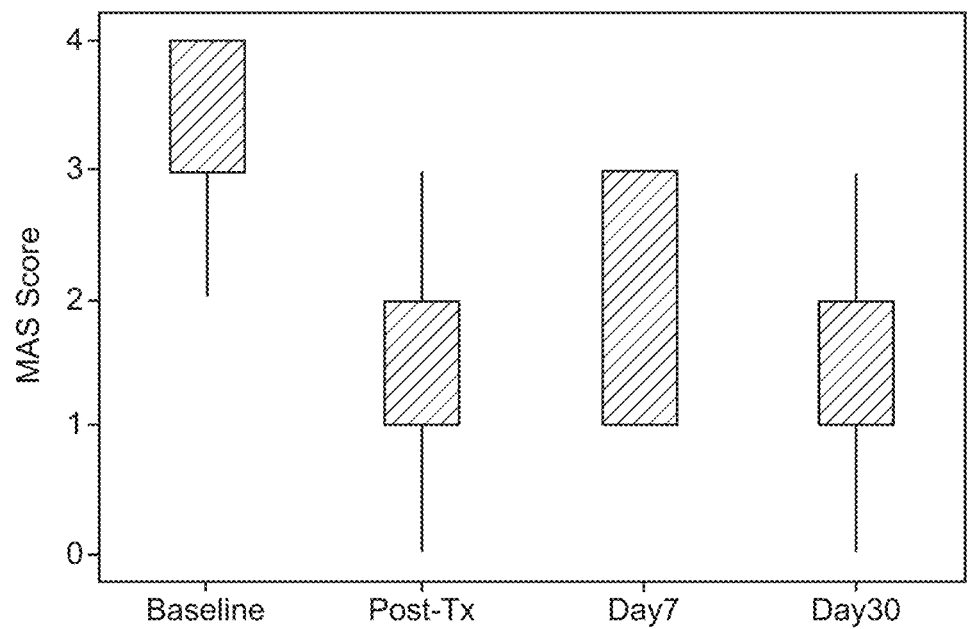
FIG. 6 shows a chart of clinical results for the distribution of MAS scores reported during a study follow-up period.

The treatment target was the peripheral musculocutaneous nerve branches, as shown at FIG. 5. The nerves were treated in a fashion to block the nerve at one or both of the shown block locations, as deemed appropriate by the investigator. Non-invasive ultrasound imaging and nerve stimulation via a transcutaneous or percutaneous method were used at the discretion of the investigator to locate the nerve(s) to be treated.

Local anesthesia was injected sub dermally with the goal of complete cutaneous anesthesia. The Cryo-Touch III probe was inserted into the epidermis and advanced to the depth of the targeted nerve. A 15-second pre-warming phase was followed by treatment delivered for 60 seconds and a 10 second warming period, completed after treatment. Collectively this is described as a treatment. After the treatment was completed, the probe was removed and inserted adjacent to form a series of treatments in a line across the pathway of the target nerve branch. See Section 4.4 for treatment data.

4. STUDY OVERVIEW 4.1 Investigational Sites

This study was conducted at two investigational sites.

4.2 Subject Accountability

Subjects were consented using an IRB approved informed consent form. Subjects who completed the screening process and met study eligibility were enrolled in the study. A Subject was deemed enrolled once treatment with the Cryo-Touch III was initiated. Nineteen Subjects were enrolled in the study. See Table 1 for Subject accountability.

TABLE 1

| Subject Accountability | | | |
|---|---|---|---|
| Subject Status | Site 21 | Site 22 | Total |
| Enrolled | 10 | 9 | 19 |
| Discontinued - subject withdrawal | 0 | 0 | 0 |
| Discontinued - investigator withdrawal | 0 | 0 | 0 |
| Subject lost to follow-up | 1 | 1 | 2 |
| Excluded for Protocol Violation | 0 | 0 | 0 |
| Total Included in Data Analysis | 10 | 9 | 19 |

No Subjects have been discontinued from the study by either Subject or investigator withdrawal, and no Subjects have been excluded from data analysis for a protocol violation. Two Subjects were lost to follow-up; one after the Day 30 visit and the other after a missed Day 56 visit. Subject accountability is 100% at the Day 7 and Day 30 follow-up visits, and 89% (17/19) at the Day 56 follow-up visit. Subjects who continued to demonstrate a treatment effect at Day 56 remained in the study and were followed every 4 weeks via telephone calls, up to 112 days or until there was no longer effect noted by the Subject. Ten Subjects were followed to Day 84, and 7 Subjects were followed to Day 112.

4.3 Demographics

Demographic information is described in Table 2 below. The average age of the 19 Subjects enrolled was 54.6 years old (standard deviation 15.6, range 22-77). Fifty-eight (58%) percent of the Subjects were male and 42% were female. The most common primary diagnosis was stroke (84%). Two Subjects had a diagnosis of traumatic brain injury (11%), and one Subject had a diagnosis of spinal cord injury (5%). Previous treatments for spasticity included physical therapy and occupational therapy, both reported as a previous treatment by 74% of Subjects. Subjects averaged 279 days of physical therapy and 266 days of occupational therapy. Other previous treatments for spasticity were intrathecal baclofen (11%), chemical neurolysis (42%) and botulinum toxin injection (74%). Three Subjects (16%) reported fitness/working out in a gym as an additional previous treatment.

TABLE 2 demographics

| | | |
|---|---|---|
| Age | Average (Standard Range | 54.6 (15.6) 22-77 |
| Gender | Male | 58% (11/19) |
| | Female | 42% (8/19) |
| Primary Diagnosis | Stroke | 84% (16/19) |
| | Traumatic Brain Injury | 11% (2/19) |
| | Other: Spinal cord injury | 5% (1/19) |
| Previous Treatments for Spasticity* | Physical Therapy | 74% (14/19) |
| | Occupational Therapy | 74% (14/19) |
| | Intrathecal Baclofen | 11% (2/19) |
| | Chemical Neurolysis | 42% (8/19) |
| | Botulinum Toxin | 74% (14/19) |
| | Other: Fitness/working | 16% (3/19) |

*Percentages add up to more than 100% because Subjects were asked to report all previous treatments.

4.4 Treatment Data

4.4.1 Analgesia/Anesthesia

The Cryo-Touch III device was used on awake subjects who were prepared with dermal anesthesia only. Local anesthesia was injected into target site with the goal of complete cutaneous anesthesia at the target treatment area prior to the treatment.

4.4.2 Treatment Algorithm

All subjects received treatments with the Cryo-Touch III® system by Myoscience, Inc. with a 6 mm uncladded cyro-probe (having three 6 mm needles, similar to what is shown in FIG. 4A). Anatomical landmarks and palpitation were used to guide treatment locations. Additionally, a combination of transcutaneous electrical nerve stimulation (TENS), percutaneous electrical nerve stimulation (PENS) and ultrasound was used as needed to provide additional treatment guidance. Treatment algorithms were consistent between sites. Subjects at Site 21 received an average of 5.4 insertions per treatment and subjects at Site 22 received an average of 3.1 insertions.

4.4.3 Target Treatment Area

See Section 3.5 above for a description of the general treatment area. Treatment approach varied between sites; both sites targeted the same nerve, but treated at different locations. At Site 21, the treatments were performed more distally, while the treatments at Site 22 were more proximal. As a result, the average depth of the nerve treated was 13.9 mm at Site 21 and 9.3 mm at Site 22.

5. SUMMARY OF RESULTS

5.1 Effectiveness Results

An effectiveness analysis was performed for all 19 Subjects. Primary and additional endpoints (see Section 3.2) were analyzed for response rates, calculated as the percentage of Subjects showing improvement of at least 1 point over baseline score. Response rates were also calculated for the percentage of Subjects showing a minimal clinically important difference (MCID) for all assessments with an established MCID or equivalent. With the exception of duration of treatment effect, all endpoints were also assessed for statistically significant improvement in scores from baseline immediately post-treatment (Post-Tx), at Day 7 and at Day 30. Statistically significant improvements were determined by testing against a null hypothesis of $H_O$: Difference=0, where the difference was calculated by subtracting the score at the follow-up visit from the score reported at baseline. A paired, two-tailed t-test was employed to test against the null hypothesis at a statistical significance level of $P<0.05$. The results of this analysis are reported below for all effectiveness endpoints. All averages calculated include the standard deviation parenthetically to better describe the statistical outcomes of this analysis.

5.1.1 Modified Ashworth Scale (MAS)

Hypertonia, as measured on the Modified Ashworth Scale (MAS), was assessed at baseline, post-treatment, Day 7 and Day 30. For the purpose of quantifying the changes measured on the MAS, this analysis treats the 6-point scale as ordinal, assigning a value of "2" to the "1+" rating and valuing the rest of the scale accordingly. MAS scores were analyzed for response rates and statistically significant improvements. There is no established MCID for MAS according to a literature search, but results were assessed for the minimal detectable change (MDC) of 1 point. See Shaw et al. (2010), BoTULS: a multicentre randomised controlled trial to evaluate the clinical effectiveness and cost-effectiveness of treating upper limb spasticity due to stroke with botulinum toxin type A. Health Technology Assessment; 14:26. FIG. 5 shows the distribution of MAS scores reported during the study follow-up period.

Seventy-four percent (74%) of Subjects reported at least a 1-point improvement in MAS at Day 7 (Table 3), the primary endpoint. MAS scores were also assessed immediately post-treatment and again at Day 30, with 89% of Subjects reporting improvement in MAS immediately post-treatment and 79% with improvement at Day 30.

TABLE 3

PERCENT OF SUBJECTS WITH IMPROVEMENT IN MAS SCORE FROM BASELINE

| ≥1 point improvement | Post-Tx | Day 7 | Day 30 |
|---|---|---|---|
| MAS | 89% (17/19) | 74% (14/19) | 79% (15/19) |

When assessed immediately post-treatment, MAS scores improved by an average of 2.1 points, representing a 64% improvement from baseline. At Day 7, Subjects had an average MAS score improvement of 1.6 points, a 48% improvement from baseline. At Day 30, Subjects had an average MAS score improvement of 1.8 points, a 55% improvement compared to baseline (Table 4).

TABLE 4

AVERAGE IMPROVEMENT IN MAS SCORE FROM BASELINE

|  | Baseline (N = 19) | Post-Tx (N = 19) | Day 7 (N = 19) | Day 30 (N = 19) |
|---|---|---|---|---|
| Average MAS Score | 3.3 | 1.3 | 1.7 | 1.5 |
| (Standard Deviation) | (0.7) | (0.8) | (0.9) | (0.9) |
| Average Point Improvement |  | 2.1 | 1.6 | 1.8 |
| (Standard Deviation) |  | (1.2) | (1.3) | (1.3) |
| P-Value |  | 1.4E−06 | 4.9E−05 | 1.7E−05 |

The point improvements from baseline at immediately post-treatment, Day 7 and Day 30 follow-ups were tested against the null hypothesis ($H_O$: Difference=0) and produced P-values of 1.4E-06, 4.9E-05 and 1.7E-05, respectively. These P-values meet the threshold of statistical significance (P<0.05) and reject the null hypothesis of zero change from baseline. The analysis shows a statistically significant improvement in the MAS scores from baseline to the follow-up assessments.

5.1.2 Tardieu Scale

Figure 7:
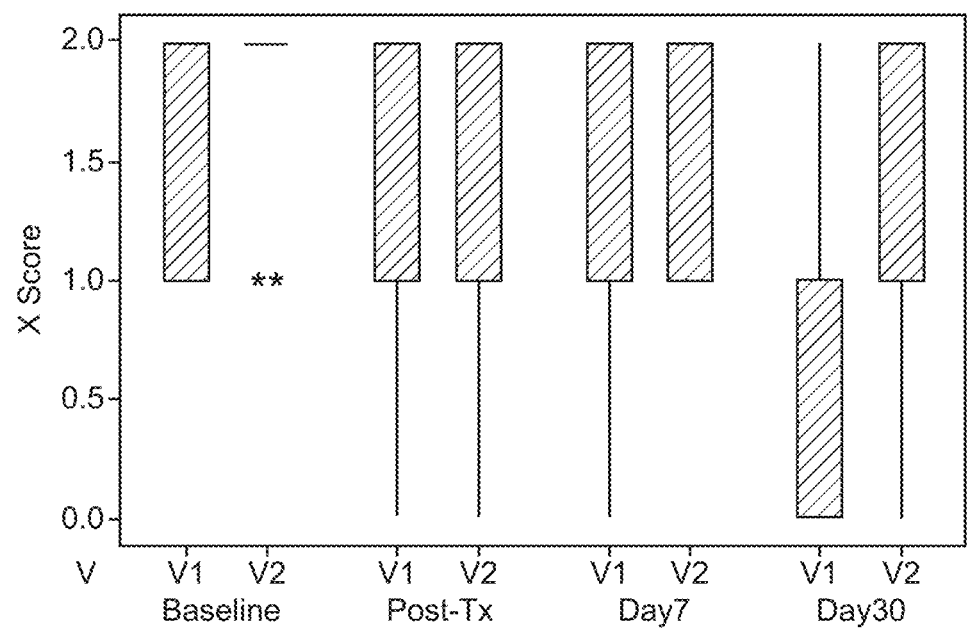
FIG. 7 shows a chart of clinical results for the distribution of reported X scores for elbow flexors at V1 and V2 during a study follow-up period.

The Tardieu Scale, completed by the investigator at baseline, immediately post-treatment, Day 7 and Day 30, encompasses a variety of joints, positions and velocities to be assessed for spasticity. This analysis focuses on the quality of muscle reaction in the elbow flexors, as measured by the X parameter on a scale from 0 (no resistance) to 4 (immovable joint). Spasticity angles are outside the scope of this analysis. Investigators assessed elbow flexors at both V1 and V2; V1 is used to assess passive range of motion while V2 is the recommended velocity for measuring spasticity of the elbow flexors. See Morris, S. (2002), Ashworth and Tardieu scales: Their clinical relevance for measuring spasticity in adult and paediatric neurological populations. Physical Therapy Reviews, 7: 53-62. The results for both velocities are described herein. There is no established MCID, MDC or equivalent for the Tardieu scale against which to measure these results. FIG. 7 shows the distribution of reported X scores for elbow flexors at V1 and V2 during study follow-up period.

When assessed at V1, 42% of Subjects showed improvement in X score immediately post-treatment. This percentage increased to 47% at Day 7 and 63% at Day 30. The results for V2 were similar, with 42% of Subjects showing at least a 1-point improvement in X score both immediately post-treatment and at Day 7. At Day 30, 47% of Subjects continued to show improvement (Table 5).

TABLE 5

PERCENT OF SUBJECTS WITH IMPROVEMENT IN TARDIEU X SCORE FROM BASELINE

| ≥1 point improvement | Post-Tx | Day 7 | Day 30 |
|---|---|---|---|
| Elbow Flexors V1: X | 42% (8/19) | 47% (9/19) | 63% (12/19) |
| Elbow Flexors V2: X | 42% (8/19) | 42% (8/19) | 47% (9/19) |

The average X score for V1 improved from baseline by an average of 0.6 points immediately post-treatment, 0.5 points at Day 7 and 0.9 points at Day 30 (Table 6). The X scores given for the V2 assessments followed a similar pattern, with Subjects recording an average improvement of 0.5 points immediately post-treatment, 0.4 points at Day 7 and 0.7 points at Day 30 (Table 7).

TABLE 6

AVERAGE IMPROVEMENT IN TARDIEU X SCORE for elbow flexors at v1 FROM BASELINE

|  | Baseline (N = 19) | Post-Tx (N = 19) | Day 7 (N = 19) | Day 30 (N = 19) |
|---|---|---|---|---|
| Average X Score at V1 | 1.7 | 1.1 | 1.2 | 0.8 |
| (Standard Deviation) | (0.4) | (0.7) | (0.7) | (0.7) |
| Average Point Improvement |  | 0.6 | 0.5 | 0.9 |
| (Standard Deviation) |  | (0.8) | (0.6) | (0.8) |
| P-Value |  | 0.00386 | 0.001466 | 0.000138 |

TABLE 7

AVERAGE IMPROVEMENT IN TARDIEU x SCORE for elbow flexors at v2 FROM BASELINE

|  | Baseline (N = 19) | Post-Tx (N = 19) | Day 7 (N = 19) | Day 30 (N = 19) |
|---|---|---|---|---|
| Average X Score at V2 | 1.9 | 1.4 | 1.5 | 1.3 |
| (Standard Deviation) | (0.3) | (0.7) | (0.5) | (0.7) |
| Average Point Improvement |  | 0.5 | 0.4 | 0.7 |
| (Standard Deviation) |  | (0.7) | (0.5) | (0.6) |
| P-Value |  | 0.004044 | 0.001966 | 0.001966 |

Score improvements for both V1 and V2 were tested against the null hypothesis (Ho: Difference=0) for statistical significance. The improvements immediately post-treatment, at Day 7 and at Day 30 for V1 scores produced P-values of 0.00386, 0.001466 and 0.000138 respectively. The same test performed on the V2 measurements produced P-values of 0.004044, 0.001966 and 0.001966 at immediately post-treatment, Day 7 and Day 30. These meet the P<0.05 significance threshold and reject the null hypothesis of zero difference, indicating the improvements seen in quality of muscle reaction, as measured by X score on the Tardieu Scale, were statistically significant for both velocities at all follow-up points.

5.1.3 Penn Spasm Score

Figure 8:
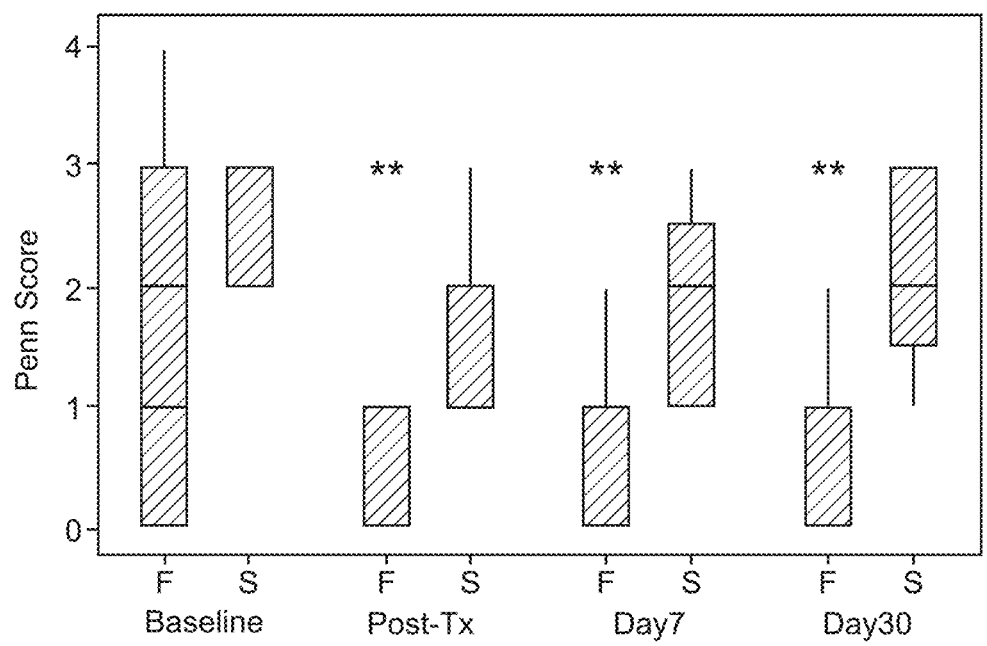
FIG. 8 shows a chart of clinical results for the distribution of Penn spasm frequency and severity scores over the study follow-up period.

The Penn Spasm Score comprises two sub-categories: Spasm frequency and spasm severity, both assessed at baseline, immediately post-treatment, Day 7 and Day 30. The Penn score uses a 5-point scale to measure spasm frequency and a 3-point scale for spasm severity. If a subject rated "0" for spasm frequency, severity was not assessed. Frequency and severity scores have been analyzed independently for response rates and statistically significant improvements. There is no established MCID, MDC or equivalent for the Penn Spasm Score. FIG. 8 shows the distribution of Penn spasm frequency and severity scores over the study follow-up period.

Immediately post-treatment, 37% of Subjects reported improvement in spasm frequency of at least 1 point on the Penn scale, while 57% reported improvement in spasm severity. At Day 7, 26% of Subjects saw improvement in spasm frequency, while 67% saw improvement in spasm severity. These rates were relatively unchanged at Day 30, with 32% of Subjects experiencing at least a 1 point improvement in frequency and 56% showing the same improvement in spasm severity (Table 8).

TABLE 8

PERCENT OF SUBJECTS WITH IMPROVEMENT
IN PENN SCORE FROM BASELINE

|  | ≥1 point improvement | | |
|---|---|---|---|
|  | Post-Tx | Day 7 | Day 30 |
| Frequency | 37% (7/19) | 26% (5/19) | 32% (6/19) |
| Severity | 57% (4/7) | 67% (6/9) | 56% (5/9) |

Subjects saw an average improvement in Penn spasm frequency score of 0.6 points immediately post-treatment, 0.5 points at Day 7 and 0.5 points at Day 30 (Table 9).

TABLE 9

AVERAGE IMPROVEMENT IN penn
frequency SCORE FROM BASELINE

|  | Baseline (N = 19) | Post-Tx (N = 19) | Day 7 (N = 19) | Day 30 (N = 19) |
|---|---|---|---|---|
| Average Penn Frequency Score | 1.3 | 0.7 | 0.7 | 0.7 |
| (Standard Deviation) | (1.5) | (1.1) | (1.0) | (1.0) |
| Average Point Improvement |  | 0.6 | 0.5 | 0.5 |
| (Standard Deviation) |  | (1.1) | (1.1) | (1.2) |
| P-Value |  | 0.044748 | 0.056167 | 0.076055 |

When tested against the null hypothesis ($H_O$: Difference=0), the improvements seen immediately post-treatment produced a P-value of 0.044748, meeting the P<0.05 significance level, while the improvements at Day 7 and Day 30 produced P-values of 0.056167 and 0.076055, both of which fail to reach the significance level. These results reject the null hypothesis for immediately post-treatment only, indicating a statistically significant improvement at this time point. The test does not reject the null hypothesis at Day 7 or Day 30; therefore, the improvements seen at Day 7 and at Day 30 are not statistically significant.

When assessed immediately post-treatment, Penn severity scores improved by an average of 0.9 points. At Day 7, Subjects averaged an improvement of 0.7 points, and at Day 30, they averaged an improvement of 0.3 points (Table 10).

TABLE 10

AVERAGE IMPROVEMENT IN penn
severity SCORE FROM BASELINE

|  | Baseline (N = 9) | Post-Tx (N = 7) | Day 7 (N = 9) | Day 30 (N = 9) |
|---|---|---|---|---|
| Average Penn Severity Score | 2.4 | 1.6 | 1.8 | 2.1 |
| (Standard Deviation) | (0.5) | (0.7) | (0.8) | (0.7) |
| Average Point Improvement |  | 0.9 | 0.7 | 0.3 |
| (Standard Deviation) |  | (0.8) | (0.8) | (0.8) |
| P-Value |  | 0.363787 | 0.362071 | 0.346165 |

These scores were tested against the null hypothesis ($H_O$: Difference=0) and produced P-values of 0.363787 for immediately post-treatment, 0.362071 at Day 7 and 0.346165 at Day 30. These values do not meet the P<0.05 significance threshold, and cannot reject the null hypothesis. Therefore, improvements in spasm severity as measured by the Penn severity scale are not statistically significant.

5.1.4 Fugl-Meyer Scale

Figure 9:
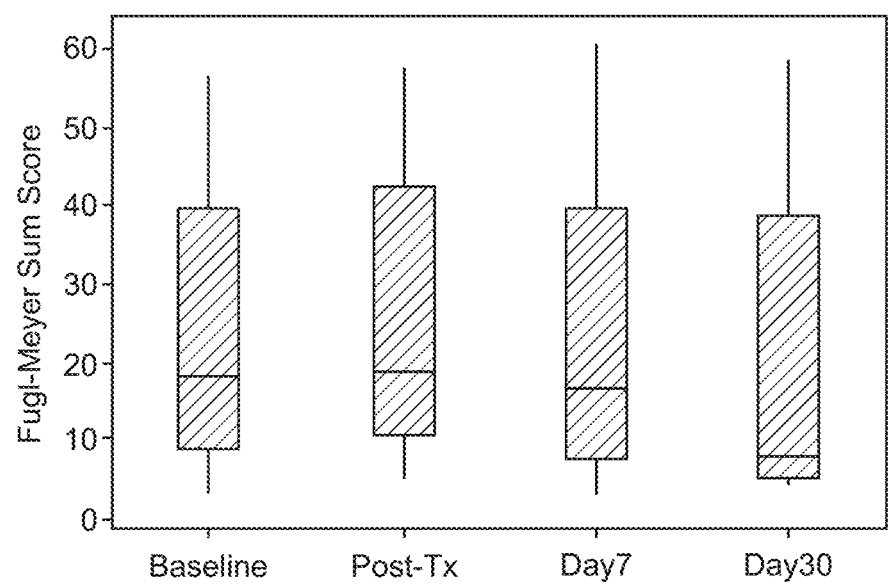
FIG. 9 shows a chart of clinical results for the distribution of sum scores reported over the study follow-up period.

The Fugl-Meyer assessment was completed for all Subjects status post stroke at baseline, immediately post-treatment, Day 7 and Day 30. A Subject's score is the sum of their ratings on each of these items, where the maximum (best) score is a 66. The MCID for Fugl-Meyer is a 5.25-point improvement in overall score, which also represents the MDC. See Page, S; Fulk, G; Boyne, P (2012), Clinically important differences for the upper-extremity Fugl-Meyer scale in people with minimal to moderate imipairment due to chronic stroke. Physical Therapy, 92: 791-798. One Subject whose primary diagnosis was not stroke was erroneously assessed using the Fugl-Meyer scale; this Subject has been excluded from the Fugl-Meyer analysis. FIG. 9 shows the distribution of sum scores reported over the study follow-up period.

Of the 16 Subjects in this study who were status post stroke, 56% saw at least a 1 point improvement in Fugl-Meyer sum score immediately post-treatment. At Day 7, 31% saw at least a 1 point improvement, and at Day 30, 31% saw improvement. A clinically important improvement of ≥6 points was seen in 19% of Subjects post-treatment and at Day 7, and in 6% of Subjects at Day 30 (Table 11).

TABLE 11

PERCENT OF SUBJECTS WITH IMPROVEMENT
IN FUGL-MEYER SUM SCORE FROM BASELINE

| Fugl-Meyer Sum Score | Post-Tx | Day 7 | Day 30 |
|---|---|---|---|
| ≥1 point improvement | 56% (9/16) | 31% (5/16) | 31% (5/16) |
| ≥6 point improvement | 19% (3/16) | 19% (3/16) | 6% (1/16) |

On average, Subjects saw minimal point improvements in Fugl-Meyer scores over the follow-up period. Immediately post-treatment, Subjects recorded an average point improvement of 2.8 points over baseline; at Day 7, the average improvement was 0.1 points, and at Day 30, Fugl-Meyer scores had worsened by an average of 2.3 points (Table 12).

TABLE 12

AVERAGE IMPROVEMENT IN FUGL-
MEYER SUM SCORE FROM BASELINE

|  | Baseline (N = 16) | Post-Tx (N = 16) | Day 7 (N = 16) | Day 30 (N = 16) |
|---|---|---|---|---|
| Average Fugl-Meyer Sum Score | 24.5 | 27.3 | 24.6 | 22.3 |
| (Standard Deviation) | (17.9) | (17.1) | (18.7) | (19.9) |
| Average Point Improvement |  | 2.8 | 0.1 | -2.3 |
| (Standard Deviation) |  | (5.3) | (7.4) | (6.7) |
| P-Value |  | 0.062186 | 0.948514 | 0.210209 |

When tested against the null hypothesis, the resulting P-values (0.062186, 0.948514, and 0.210209) failed to meet the P<0.05 significance threshold for rejecting the null hypothesis. The results show no statistically significant improvements in Fugl-Meyer scores at any follow-up point.

5.1.5 Mean Spasticity Numerical Rating Scale (NRS)

Figure 10:
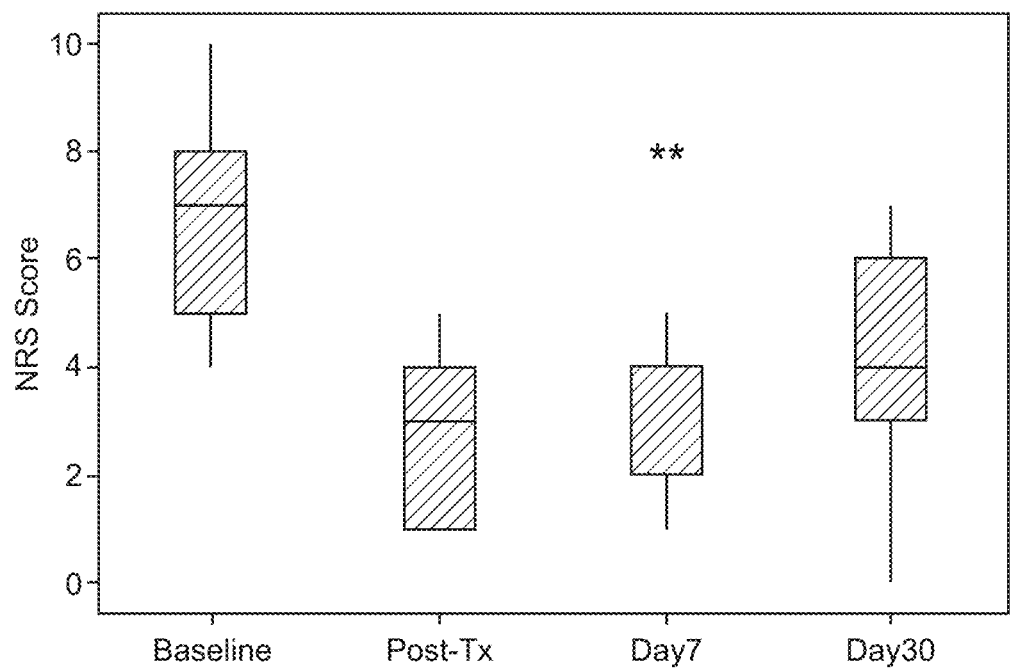
FIG. 10 shows a chart of clinical results for the distribution of NRS scores over study follow-up period.

Subjects completed the spasticity numerical rating scale (NRS) at baseline, immediately post-treatment, Day 7 and again at Day 30. The NRS is an 11-point scale from 0 to 10, where lower scores represent less spasticity. The NRS results have been analyzed for response rates, statistically significant improvements, and clinically important improvements. A clinically important difference (CID) has been defined as a 30% improvement, while the MCID is an 18% improvement in NRS score. See Farrar et al. (2008), Validity, reliability, and clinical importance of change in a 0-10 numeric rating scale measure of spasticity; a post hoc analysis of a randomized, double-blind, placebo-controlled trial. Clinical Therapeutics, 30:5: 974-985. FIG. 10 shows the distribution of NRS scores over study follow-up period.

Immediately post-treatment, 89% of Subjects reported at least a 1 point improvement in NRS score from baseline. At Day 7, 79% of Subjects reported improvement, and at Day 30, 79% reported continued improvement in spasticity as measured by the NRS. Results were also assessed for the MCID and CID. An 18% improvement, the MCID, was seen in 89% of Subjects immediately post-treatment, 79% at Day 7 and 68% at Day 30. The CID of a 30% improvement was seen in 84% of Subjects immediately post-treatment, 68% at Day 7 and 63% at Day 30 (Table 13).

TABLE 13

PERCENT OF SUBJECTS WITH IMPROVEMENT IN NRS SCORE FROM BASELINE

| NRS | Post-Tx | Day 7 | Day 30 |
|---|---|---|---|
| ≥1 point improvement | 89% (17/19) | 79% (15/19) | 79% (15/19) |
| 18% improvement | 89% (17/19) | 79% (15/19) | 68% (13/19) |
| 30% improvement | 84% (16/19) | 68% (13/19) | 63% (12/19) |

On the average, Subjects experienced consistent and sustained point improvements on the NRS. Immediately post-treatment, Subjects reported an average point improvement of 4.0, a 60% improvement from baseline score. Subjects saw an average point improvement of 3.2 points at Day 7 and 2.5 points at Day 30 (Table 14).

TABLE 14

AVERAGE IMPROVEMENT IN NRS SCORE FROM BASELINE

| | Baseline (N = 19) | Post-Tx (N = 19) | Day 7 (N = 19) | Day 30 (N = 18) |
|---|---|---|---|---|
| Average NRS Score | 6.7 | 2.7 | 3.5 | 4.2 |
| (Standard Deviation) | (2.0) | (1.5) | (1.6) | (1.8) |
| Average Point Improvement | | 4.0 | 3.2 | 2.5 |
| (Standard Deviation) | | (2.3) | (2.3) | (2.0) |
| P-Value | | 8.4E−07 | 1.4E−05 | 3.9E−05 |

These improvements were tested for significance against the null hypothesis ($H_O$: Difference=0) and produced P-values of 8.4E-07, 1.4E-05 and 3.9E-05 for immediately post-treatment, Day 7 and Day 30, respectively. These P-values exceed the threshold for significance (P<0.05) and reject the null hypothesis, indicating the improvements seen in spasticity as measured by the NRS are statistically significant at all follow-up points.

5.1.6 Visual Analog Scale (VAS)

Figure 11:
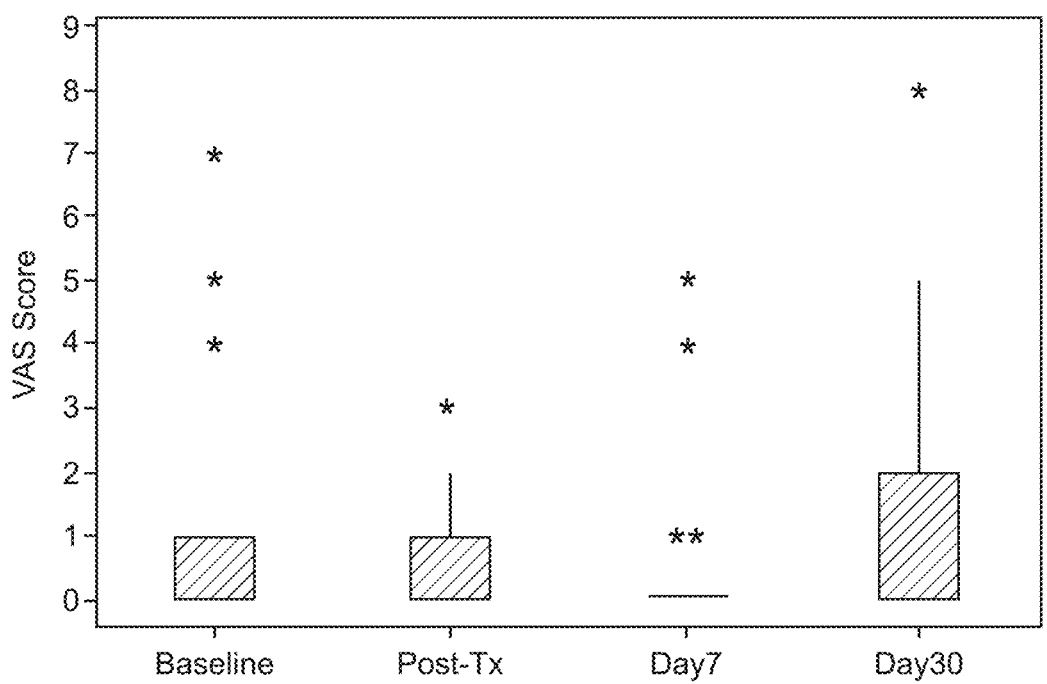
FIG. 11 shows a chart of clinical results for the distribution of VAS scores reported during study follow-up period.

Subjects completed the visual analog scale (VAS) at baseline, immediately post-treatment, Day 7 and Day 30 to report pain levels on the 0-10 scale. This analysis looks at response rates, average improvements, and assessed against the MCID of a 1.3 point improvement on the 0-100 mm scale, which corresponds to a ≥2 point improvement in VAS score. See Gallagher, J., Liebman, M., and Bijur, P. (2001). Prospective validation of clinically important changes in pain severity measured on visual analog scale. Ann Emerg Med. 38:6; 633-638. FIG. 11 shows the distribution of VAS scores reported during study follow-up period.

When assessed immediately post-treatment, 26% of Subjects reported an improvement in VAS of at least 1 point; at Day 7, 11% of Subjects reported improvement, and by Day 30, only 5% reported improvement in pain as measured by VAS (Table 15).

TABLE 15

PERCENT OF SUBJECTS WITH IMPROVEMENT IN VAS SCORE FROM BASELINE

| VAS | Post-Tx | Day 7 | Day 30 |
|---|---|---|---|
| ≥1 point improvement | 26% (5/19) | 11% (2/19) | 5% (1/19) |
| ≥2 point improvement | 16% (3/19) | 5% (1/19) | 5% (1/19) |

The average VAS score reported did not change substantially over the course of the follow-up period; Subjects saw VAS scores improve by an average of 0.4 points immediately post-treatment and 0.6 points by Day 7. At Day 30, VAS scores worsened by an average of 0.2 points (Table 16).

TABLE 16

AVERAGE IMPROVEMENT IN VAS SCORE FROM BASELINE

| | Baseline (N = 19) | Post-Tx (N = 19) | Day 7 (N = 19) | Day 30 (N = 19) |
|---|---|---|---|---|
| Average VAS Score | 1.0 | 0.4 | 0.6 | 1.2 |
| (Standard Deviation) | (2.0) | (0.8) | (1.4) | (2.1) |
| Average Point Improvement | | 0.5 | 0.4 | −0.2 |
| (Standard Deviation) | | (1.5) | (1.3) | (0.8) |
| P-Value | | 0.153832 | 0.260688 | 0.259012 |

Changes in VAS scores at each follow-up point were tested for statistical significance against the null hypothesis ($H_O$: Difference=0) and produced P-values that failed to meet the P<0.05 threshold (0.153832, 0.260688, and 0.259012). Therefore, the results show no statistically significant improvement in VAS scores.

5.1.7 Duration of Treatment Effect

Subjects were asked to report the duration of treatment effect at Day 7, Day 30, and Day 56. Subjects could designate their results as "effect" "no effect" or "no longer effective". Subjects reporting "effect" at Day 56 were followed to Day 84; those with effect at Day 84 continued to be followed to Day 112. All percentages are calculated out of the study population (N=19) rather than the completed population at each follow-up point as not all subjects were followed beyond Day 56. Table 17 below shows the percentage of subjects with effect lasting to a given follow-up point. At Day 7, 79% of Subjects reported effect from the treatment. At Day 30, 89% of Subjects reported continued effect from treatment, and at Day 56, 53% of Subjects reported effect. Ten Subjects were followed beyond Day 56; at Day 84, 37% of Subjects reported effect, and at Day 112, 32% of Subjects reported effect. The two Subjects lost to follow-up after Day 30 reported effect at their Day 30 visit.

TABLE 17 subject-reported Duration of treatment effect

| | Day 7 | Day 30 | Day 56 | Day 84 | Day 112 |
|---|---|---|---|---|---|
| % with Effect | 79% (15/19) | 89% (17/19) | 53% (10/19) | 37% (7/19) | 32% (6/19) |

5.2 Subject Experience

Subjects completed the post-treatment questionnaire at the Day 7, Day 30 and Day 56 visits. The questionnaire assessed Subject Satisfaction, Subject experience with anticipated observations and Subject's pain from treatment. The responses for Subject Satisfaction are shown in Table 18 below. At Day 7, 94% of Subjects said they would recommend the treatment to a family member; at Day 30, this number was 79%, and at Day 56, this was 76%. Similarly, 89% of Subjects indicated they would have the treatment again when asked at Day 7; at Day 30, this was 84%, and at Day 56 this was 88%.

TABLE 18

Subject Satisfaction

|  | Day 7 | Day 30 | Day 56 |
|---|---|---|---|
| Would you recommend this treatment to a family member? (% Yes) | 89% (17/19) | 79% (15/19) | 76% (13/17) |
| Would you have this treatment again? (% Yes) | 89% (17/19) | 84% (16/19) | 88% (15/17) |

Subject experience with anticipated observations was assessed, and these results are described in Table 19 below. The data below reflect how the Subjects responded to the question and not the data documented during physical assessment, which can be found in Table 21 in Section 5.3 below.

TABLE 19

Subject Reported anticipated observations

|  |  | Day 7 | Day 30 | Day 56 |
|---|---|---|---|---|
| Did the subject report any anticipated observations? (% Yes) |  | 16% (3/19) | 5% (1/19) | 0% (0/17) |
| If yes, how much did they/it impact subject's daily routine? | 1 (AO had very negative impact) | 0% (0/19) | 0% (0/19) | 0% (0/17) |
|  | 2 | 5% (1/19) | 0% (0/19) | 0% (0/17) |
|  | 3 | 11% (2/19) | 5% (1/19) | 0% (0/17) |
|  | 4 | 0% (0/19) | 0% (0/19) | 0% (0/17) |
|  | 5 (No impact at all) | 0% (0/19) | 0% (0/19) | 0% (0/17) |

Subjects were also asked if pain was present from treatment and if so, to rate it on a 1-5 scale. No Subjects reported pain from treatment at either time point assessed. These results are shown below in Table 20.

TABLE 20

Subject reported pain from treatment

|  |  | Day 7 | Day 30 | Day 56 |
|---|---|---|---|---|
| Is there any pain present from treatment? (% Yes) |  | 0% (0/19) | 0% (0/19) | 0% (0/17) |
| If yes, enter scale | 1 (Not at all painful) | 0% (0/19) | 0% (0/19) | 0% (0/17) |
|  | 2 | 0% (0/19) | 0% (0/19) | 0% (0/17) |
|  | 3 | 0% (0/19) | 0% (0/19) | 0% (0/17) |
|  | 4 | 0% (0/19) | 0% (0/19) | 0% (0/17) |
|  | 5 (Very painful) | 0% (0/19) | 0% (0/19) | 0% (0/17) |

5.3 Anticipated Observations

The Cryo-Touch III® involves percutaneous access to subcutaneous tissue using a needle, use of dermal anesthesia and focused cold therapy treating the targeted nerve. Passage of a needle into the skin, delivery of local anesthesia and the nature of focused cold therapy are all known to be associated with the risks listed below. These risks were collected by the investigator as anticipated observations independent of adverse events. These reactions do not typically require medical intervention on the part of the investigator and are usually transient. In the event that the anticipated observations listed below exceed the expected response to the treatment, either in severity or in duration, they were reported as Adverse Events.

Ecchymosis (bruising)
Edema (swelling)
Erythema (redness or inflammation)
Pain and/or tenderness
Localized dysesthesia (altered sensation)
Thermal injury to the skin, skin lesions, hyper or hypo pigmentation secondary to skin injury
Dimpling of skin Anticipated observations were assessed at baseline, Day 7, Day 30, and Day 56. The occurrence of these anticipated observations are shown below in Table 21. The most frequently reported observation was bruising, with 37% (7/19) of Subjects reporting mild bruising and 5% (1/19) reporting moderate bruising at Day 7. All bruising had resolved by Day 30. Tingling was reported by one Subject (5%) at Day 7 and by another Subject at Day 30. Two cases of mild swelling (11%) were reported at Day 7, both of which resolved by Day 30. Two cases of mild pain (11%) were also reported at Day 7, and resolved by Day 30. One mild case of itching (5%) was reported at Day 30. No observations were reported at Day 56.

TABLE 21

ANTICIPATED OBSERVATIONS REPORTED AT TREATMENT SITE

|  | Day 7 | | | Day 30 | | | Day 56 | | |
|---|---|---|---|---|---|---|---|---|---|
|  | Mild | Mod | Sev | Mild | Mod | Sev | Mild | Mod | Sev |
| Bruising | 37% (7/19) | 5% (1/19) | 0% | 0% | 0% | 0% | 0% | 0% | 0% |
| Swelling | 11% (2/19) | 0% | 0% | 0% | 0% | 0% | 0% | 0% | 0% |
| Tingling | 5% (1/19) | 0%) | 0% | 5% (1/19) | 0% | 0% | 0% | 0% | 0% |
| Local Pain | 11% (2/19) | 0% | 0% | 0% | 0% | 0% | 0% | 0% | 0% |
| Itching | 0% | 0% | 0% | 5% (1/19) | 0% | 0% | 0% | 0% | 0% |
| Redness/ Inflammation | 0% | 0% | 0% | 0% | 0% | 0% | 0% | 0% | 0% |
| Erosion | 0% | 0% | 0% | 0% | 0% | 0% | 0% | 0% | 0% |
| Crusting | 0% | 0% | 0% | 0% | 0% | 0% | 0% | 0% | 0% |

TABLE 21-continued

ANTICIPATED OBSERVATIONS REPORTED AT TREATMENT SITE

|  | Day 7 | | | Day 30 | | | Day 56 | | |
| --- | --- | --- | --- | --- | --- | --- | --- | --- | --- |
|  | Mild | Mod | Sev | Mild | Mod | Sev | Mild | Mod | Sev |
| Dimpling | 0% | 0% | 0% | 0% | 0% | 0% | 0% | 0% | 0% |
| Hyperpigmentation | 0% | 0% | 0% | 0% | 0% | 0% | 0% | 0% | 0% |
| Hypopigmentation | 0% | 0% | 0% | 0% | 0% | 0% | 0% | 0% | 0% |

5.4 Adverse Events

An adverse events is any unfavorable or unintended sign (e.g., abnormal laboratory finding), symptom or disease temporally associated with the use of a device without judgment of causality. These adverse events are shown below in Table 22. No unanticipated adverse device effects (UADEs) were reported in the conduct of this study. An UADE is any SAE not previously identified in nature, severity or degree of incidence in the investigational plan, or application, or any other unanticipated serious problem associated with a device that relates to the rights, safety, or welfare of subjects. See 21 CFR §812.3. Six of the 19 Subjects, or 32% of the study population, have reported a total of seven adverse events.

TABLE 22

Summary of device- or procedure-related adverse events in subjects treated with the cleared Cryo-Touch III ® device

| Subject ID | Description of AE | Severity | Action | Outcome | Relation to Device |
| --- | --- | --- | --- | --- | --- |
| 22-003 | Soreness at triceps, left elbow | Mild | None | Resolved | Possible |
| 21-005 | Temporary increase in spasticity of treated extremity | Mild | None | Resolved | None, possible relation to procedure |
| 21-009 | Colon Cancer* | Severe | Surgery, medication | Unchanged | None |
| 22-006 | Cellulitis right side of scrotum and groin* | Severe | Medication | Resolved | None |
| 21-010 | Seizure | Moderate | None | Resolved | None |
| 22-002 | Edema left clavicular | Mild | None | Unchanged | None |
| 22-002 | Blepharoplasty | Moderate | Surgery | Resolved | None |

*Indicates Serious Adverse Event

Two Serious Adverse Events (SAEs) were reported, both rated by the investigator as unrelated to study device or procedure. One Subject was hospitalized due to colon cancer one month after receiving treatment. The Subject received surgical and medical intervention, and exited the study with the adverse event ongoing. Another Subject was hospitalized due to cellulitis of the right scrotum and groin. The Subject received intravenous and oral antibiotics, and symptoms of pain resolved 8 days after onset.

Two reported adverse events were rated by the investigator as possibly related to either study device or procedure. Both of these events were rated as mild by the investigator, and resolved within one day of onset. One Subject reported a temporary increase in spasticity of the treated extremity due to noxious stimuli following treatment. The Subject was seen in office by the investigator the following day and reported that the event had resolved within 12 hours. The Subject indicated the desire to continue in the study. After evaluation, the investigator noted the results of the treatment were still effective and no further intervention or change in treatment was necessary. The investigator assessed the event as unrelated to study device but possibly related to procedure. Another Subject reported mild soreness at the treatment site and difficulty with the triceps and elbow on the day of treatment. The Subject reported the event resolved within a day, and no intervention was required. The investigator assessed the Subject and rated the event as possibly related to study device and procedure.

5.5 Deviations from the Investigational Plan

Investigator deviations from the investigational plan were reported to the Sponsor on study case report forms. No deviations were necessary to protect the life or well-being of a Subject in an emergency, nor did any deviation affect the scientific soundness of the investigational plan or the rights, safety, or welfare of the Subjects. The most commonly reported deviation (18 reported) was a follow-up out of window due to scheduling issues; this was due in part to the Day 7 follow-up visits at site 22 were due in on or near the 4th of July holiday. There were three eligibility-related deviations reported as well, both for Subjects who had received an injection to the upper limb within the last 4 months. There was one follow-up not done; this was reported for Subject 21-009 at the Day 56 visit. This Subject was later designated as lost to follow-up. Deviations are listed in Table 23 below.

TABLE 23

Reported deviations from the investigational plan

| Description | # of Deviations |
| --- | --- |
| Follow-up out of window due to scheduling issues | 18 |
| Eligibility criteria not met: Injection to the upper limb within the last 4 months | 3 |
| Follow-up not done | 1 |

5.6 Device Malfunctions

There were 2 device malfunctions reported summarized in Table 24 below. None of these were considered to have an impact on the Subject or on the integrity of the study.

TABLE 24

Reported deviations from the investigational plan

| Description | # of Malfunctions |
|---|---|
| Replace cartridge and treatment interrupted error message | 1 |
| Disable button inadvertently depressed | 1 |

6. CONCLUSION

The final study data provides support for the safety and effectiveness of the Cryo-Touch III® device for the temporary relief of symptoms in the upper arm in Subjects with upper limb spasticity.

The primary endpoint results are as follows:
 At Day 7, 74% of Subjects reported ≥1 point improvement in MAS score for muscle tone and spasticity caused by hypertonia of the upper arm.

The secondary endpoint results are as follows:
 At Day 7, 74% of Subjects reported ≥1 point improvement in spasticity as measured by the Tardieu Scale at V1 and 72% reported ≥1 point improvement at V2. There is no established MCID, MDC or equivalent for the Tardieu Scale.
 At Day 7, 26% of Subjects reported ≥1 point improvement in spasm frequency and 67% reported ≥1 point improvement in spasm severity as measured by the Penn Spasm Score. There is no established MCID, MDC or equivalent for the Penn Spasm Score.
 At Day 7, 31% of Subjects reported ≥1 point improvement and 19% of Subjects reported a clinically important difference (≥6 point improvement) in upper extremity motor recovery as measured by the Fugl-Meyer Scale (post stroke Subjects only).
 At Day 7, 79% of Subjects assessed a ≥1 point improvement and 79% also assessed a clinically important difference (18% improvement) in Mean Spasticity Numerical Rating Scale (NRS) score.
 At Day 7, 11% of Subjects reported a ≥1 point improvement and 11% reported a clinically important difference (≥2 point improvement) in pain as assessed by visual analog scale (VAS).
 At Day 30, 89% of Subjects reported continued effect from treatment, and 53% reported effect at Day 56.

Additional assessment results are as follows:
 At Day 7, 89% of Subjects said they would recommend the treatment to a family member.
 At Day 7, 89% of Subjects said they would have the treatment again if available.

Safety measure results are as follows:
 No device related SAEs or UADEs were reported in this study.

APPENDIX A

Site Comparison

An effectiveness analysis was performed independently for the two sites, and the results were compared. All differences were assessed for statistical significance using a two-tailed t-test to measure the null hypothesis $H_O$: Site 21=Site 22 against a significance level of P<0.05. The appropriate variance was determined using Levene's test. There were significant differences between the sites' results in several measures. Tables 1-13A below show the effectiveness results for each site and the p-values from the t-test. A p-value less than 0.05 indicates a statistically significant difference between sites.

TABLE 1A

PERCENT OF SUBJECTS WITH IMPROVEMENT IN MAS SCORE FROM BASELINE

| MAS | | Post-Tx | Day 7 | Day 30 |
|---|---|---|---|---|
| ≥1 point improvement | Site 21 | 100% (10/10) | 100% (10/10) | 100% (10/10) |
| | Site 22 | 78% (7/9) | 44% (4/9) | 56% (5/9) |

TABLE 2a

AVERAGE IMPROVEMENT IN MAS SCORE FROM BASELINE

| | | Baseline | Post-Tx | Day 7 | Day 30 |
|---|---|---|---|---|---|
| Average MAS Score (Standard Deviation) | Site 21 | 3.7 (0.5) | 0.9 (0.5) | 1.0 (0) | 0.8 (0.4) |
| | Site 22 | 2.9 (0.6) | 1.7 (0.8) | 2.4 (0.7) | 2.2 (0.8) |
| | P-Value | 0.0046 | 0.0340 | 0.0003 | 0.0007 |
| Average Pt Improvement (Standard Deviation) | Site 21 | | 2.8 (0.7) | 2.7 (0.5) | 2.9 (0.5) |
| | Site 22 | | 1.2 (1.1) | 0.4 (0.8) | 0.7 (0.9) |
| | P-Value | | 0.0033 | 2.1E−06 | 1.3E−05 |

TABLE 3A

PERCENT OF SUBJECTS WITH IMPROVEMENT IN TARDIEU X SCORE FROM BASELINE

| ≥1 point improvement | | Post-Tx | Day 7 | Day 30 |
|---|---|---|---|---|
| Elbow Flexors V1: X | Site 21 | 50% (5/10) | 70% (7/10) | 70% (7/10) |
| | Site 22 | 33% (3/9) | 22% (2/9) | 56% (5/9) |
| Elbow Flexors V2: X | Site 21 | 80% (8/10) | 80% (8/10) | 80% (8/10) |
| | Site 22 | 0% (0/9) | 0% (0/9) | 11% (1/9) |

TABLE 4A

AVERAGE IMPROVEMENT IN TARDIEU X SCORE for elbow flexors at v1 FROM BASELINE

| | | Baseline | Post-Tx | Day 7 | Day 30 |
|---|---|---|---|---|---|
| Average X Score at V1 (Standard Deviation) | Site 21 | 1.5 (0.5) | 0.7 (0.5) | 0.7 (0.5) | 0.5 (0.5) |
| | Site 22 | 2.0 (0) | 1.6 (0.7) | 1.8 (0.4) | 1.2 (0.8) |
| | P-Value | 0.0114 | 0.0072 | 0.0001 | 0.0355 |
| Average Point Improvement (Standard Deviation) | Site 21 | | 0.8 (0.9) | 0.8 (0.6) | 1.0 (0.8) |
| | Site 22 | | 0.4 (0.7) | 0.2 (0.4) | 0.8 (0.8) |
| | P-Value | | 0.3664 | 0.0355 | 0.5652 |

TABLE 5A

AVERAGE IMPROVEMENT IN TARDIEU x SCORE for elbow flexors at v2 FROM BASELINE

| | | Baseline | Post-Tx | Day 7 | Day 30 |
|---|---|---|---|---|---|
| Average X Score at V2 (Standard Deviation) | Site 21 | 1.8 (0.4) | 0.8 (0.4) | 1.0 (0) | 0.8 (0.4) |
| | Site 22 | 2.0 (0) | 2.0 (0) | 2.0 (0) | 1.8 (0.6) |
| | P-Value | 0.1740 | 1.6E−07 | X | 0.0012 |
| Average Point | Site 21 | | 1.0 (0.6) | 0.8 (0.4) | 1.0 (0.6) |

TABLE 5A-continued

AVERAGE IMPROVEMENT IN TARDIEU x SCORE for elbow flexors at v2 FROM BASELINE

|  |  | Baseline | Post-Tx | Day 7 | Day 30 |
|---|---|---|---|---|---|
| Improvement (Standard Deviation) | Site 22 P-Value |  | 0 (0) 0.0011 | 0 (0) 2.7E−05 | 0.2 (0.6) 0.0212 |

TABLE 6A

PERCENT OF SUBJECTS WITH IMPROVEMENT IN PENN SCORE FROM BASELINE

| ≥1 point improvement |  | Post-Tx | Day 7 | Day 30 |
|---|---|---|---|---|
| Frequency | Site 21 | 10% (1/10) | 10% (1/10) | 10% (1/10) |
|  | Site 22 | 67% (6/9) | 44% (4/9) | 56% (5/9) |

Penn severity could not be compared between sites as there were no Subjects with severity scores at Site 21. See Section 5.1.3 above.

TABLE 7A

AVERAGE IMPROVEMENT IN penn frequency SCORE FROM BASELINE

|  |  | Baseline | Post-Tx | Day 7 | Day 30 |
|---|---|---|---|---|---|
| Average Penn Frequency Score (Standard Deviation) | Site 21 | 0.1 (0.3) | 0 (0) | 0 (0) | 0 (0) |
|  | Site 22 | 2.6 (1.3) | 1.4 (1.3) | 1.6 (0.8) | 1.6 (0.8) |
|  | P-Value | 0.0005 | 0.0117 | 3.2E−05 | 3.2E−05 |
| Average Point Improvement (Standard Deviation) | Site 21 |  | 0.1 (0.3) | 0.1 (0.3) | 0.1 (0.3) |
|  | Site 22 |  | 1.1 (1.4) | 1.0 (1.4) | 1.0 (1.6) |
|  | P-Value |  | 0.0861 | 0.1128 | 0.1455 |

Penn severity could not be compared between sites as there were no Subjects with severity scores at Site 21. See Section 5.1.3 above.

TABLE 8A

PERCENT OF SUBJECTS WITH IMPROVEMENT IN FUGL-MEYER SUM SCORE FROM BASELINE

| Fugl-Meyer |  | Post-Tx | Day 7 | Day 30 |
|---|---|---|---|---|
| ≥1 point improvement | Site 21 | 38% (3/8) | 13% (1/8) | 13% (1/8) |
|  | Site 22 | 75% (6/8) | 50% (4/8) | 50% (4/8) |
| ≥6 point improvement | Site 21 | 13% (1/8) | 0% (0/8) | 0% (0/8) |
|  | Site 22 | 25% (2/8) | 38% (3/8) | 13% (1/8) |

TABLE 9A

AVERAGE IMPROVEMENT IN FUGL-MEYER SUM SCORE FROM BASELINE

|  |  | Baseline | Post-Tx | Day 7 | Day 30 |
|---|---|---|---|---|---|
| Average Fugl-Meyer Sum Score (Standard Deviation) | Site 21 | 10.6 (5.1) | 12.6 (5.0) | 8.5 (4.2) | 4.9 (0.3) |
|  | Site 22 | 38.4 (15.2) | 41.9 (11.6) | 40.8 (12.8) | 39.6 (13.7) |
|  | P-Value | 0.0004 | 2.6E−05 | 1.9E−05 | 0.0003 |
| Average Point Improvement (Standard Deviation) | Site 21 |  | 2 (4.1) | −2.1 (5.5) | −5.8 (5.1) |
|  | Site 22 |  | 3.5 (6.1) | 2.4 (8.2) | 1.3 (6.2) |
|  | P-Value |  | 0.6001 | 0.2504 | 0.0365 |

TABLE 10A

PERCENT OF SUBJECTS WITH IMPROVEMENT IN NRS SCORE FROM BASELINE

| NRS |  | Post-Tx | Day 7 | Day 30 |
|---|---|---|---|---|
| ≥1 point improvement | Site 21 | 100% (10/10) | 80% (8/10) | 80% (8/10) |
|  | Site 22 | 78% (7/9) | 78% (7/9) | 78% (7/9) |
| 18% improvement | Site 21 | 100% (10/10) | 80% (8/10) | 70% (7/10) |
|  | Site 22 | 78% (7/9) | 78% (7/9) | 67% (6/9) |
| 30% improvement | Site 21 | 100% (10/10) | 70% (7/10) | 70% (7/10) |
|  | Site 22 | 67% (6/9) | 67% (6/9) | 56% (5/9) |

TABLE 11A

AVERAGE IMPROVEMENT IN NRS SCORE FROM BASELINE

|  |  | Baseline | Post-Tx | Day 7 | Day 30 |
|---|---|---|---|---|---|
| Average NRS Score (Standard Deviation) | Site 21 | 6.9 (2.1) | 2 (1.3) | 3.5 (2.0) | 4.7 (1.6) |
|  | Site 22 | 6.4 (1.8) | 3.4 (1.4) | 3.4 (1.0) | 3.6 (1.9) |
|  | P-Value | 0.6387 | 0.0406 | 0.9439 | 0.1964 |
| Average Point Improvement (Standard Deviation) | Site 21 |  | 4.9 (1.8) | 3.4 (2.3) | 2.2 (1.7) |
|  | Site 22 |  | 3.0 (2.4) | 3.0 (2.3) | 2.9 (2.2) |
|  | P-Value |  | 0.0817 | 0.7246 | 0.4777 |

TABLE 12A

PERCENT OF SUBJECTS WITH IMPROVEMENT IN VAS SCORE FROM BASELINE

| VAS |  | Post-Tx | Day 7 | Day 30 |
|---|---|---|---|---|
| ≥1 point improvement | Site 21 | 0% (0/10) | 0% (0/10) | 0% (0/10) |
|  | Site 22 | 56% (5/9) | 22% (2/9) | 11% (1/9) |
| ≥2 point improvement | Site 21 | 0% (0/10) | 0% (0/10) | 0% (0/10) |
|  | Site 22 | 33% (3/9) | 11% (1/9) | 11% (1/9) |

TABLE 13A

AVERAGE IMPROVEMENT IN VAS SCORE FROM BASELINE

|  |  | Baseline | Post-Tx | Day 7 | Day 30 |
|---|---|---|---|---|---|
| Average VAS Score (Standard Deviation) | Site 21 | 0 (0) | 0.1 (0.3) | 0 (0) | 0 (0) |
|  | Site 22 | 2 (2.5) | 0.8 (1.0) | 1.2 (1.8) | 2.4 (2.4) |
|  | P-Value | 0.0531 | 0.0772 | 0.0597 | 0.0208 |
| Average Point Improvement (Standard Deviation) | Site 21 |  | −0.1 (0.3) | 0 (0) | 0 (0) |
|  | Site 22 |  | 1.2 (1.9) | 0.8 (1.9) | −0.4 (1.1) |
|  | P-Value |  | 0.0901 | 0.2309 | 0.2721 |

Other variations are within the spirit of the present disclosure. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

What is claimed is:

1. A method for alleviating spasticity of a skeletal muscle in a limb of a patient, the skeletal muscle having an associated motor nerve, the method comprising:
    positioning a distal end of a cryogenic cooling needle probe proximal to the motor nerve in the limb of the patient, the cryogenic cooling needle probe having at least one needle with a lumen; and
    delivering a treatment to a target tissue with the cryogenic cooling needle probe, the treatment comprising a cooling phase where cooling fluid flows into the needle lumen so that liquid from the cooling flow vaporizes within the needle lumen to provide cooling to the motor nerve such that spasticity of the skeletal muscle in the limb of the patient is mitigated while maintaining intentional motor control of the skeletal muscle.

2. The method of claim 1, further comprising providing a degree of skin warming throughout the delivery of the treatment.

3. The method of claim 2, wherein the degree of skin warming comprises 28-42° C. of skin warming throughout the treatment.

4. The method of claim 1, wherein the cryogenic cooling needle probe further comprises a heating element coupled with a proximal portion of the at least one needle; and wherein the treatment further comprises at least one heating phase.

5. The method of claim 4, wherein the at least one heating phase comprises a pre-heat phase with the heating element before the cooling phase.

6. The method of claim 5, wherein the pre-heat phase has a duration of 2-20 seconds.

7. The method of claim 5, wherein the cooling phase has a duration of 15-120 seconds after the pre-heat phase.

8. The method of claim 7, wherein the at least one heating phase further comprises a post-heat phase.

9. The method of claim 8, wherein the post-heat phase has a duration of 5-15 seconds.

10. The method of claim 1, wherein the at least one needle comprises a length of 10-20 mm.

11. The method of claim 1, wherein the cryogenic cooling needle probe comprises a pair of needles spaced apart such that one needle is placed on one side of the motor nerve and the other needle is placed on an opposite side of the motor nerve.

12. The method of claim 1, wherein one or a combination of transcutaneous electrical nerve stimulation, percutaneous electrical nerve stimulation, and ultrasound is used to locate the motor nerve.

13. The method of claim 1, wherein during the cooling phase the cryogenic cooling needle probe generates a cryozone having a volume of 65-125 $mm^3$.

14. The method of claim 1, wherein the at least one needle comprises a length of 30-100 mm.

15. A method for alleviating spasticity of a skeletal muscle having an associated motor nerve, the method comprising:
    positioning a distal end of a cryogenic cooling needle probe proximal to the motor nerve such that a first needle of the cryogenic cooling needle probe having a first lumen is proximal to one side of the motor nerve and a second needle of the cryogenic cooling needle probe spaced apart from the first needle and having a second lumen is proximal to an opposite side of the motor nerve so as to straddle the motor nerve with the first and second needles, wherein the first needle and the second needle are spaced apart in a range of 3 mm to 7 mm;
    delivering a treatment to a target tissue with the cryogenic cooling needle probe, the treatment comprising a cooling phase where cooling fluid flows into each of the first and second needle lumens so that liquid from the cooling flow vaporizes within each of the first and second needle lumens to provide cooling to the motor nerve such that spasticity of the skeletal muscle is mitigated.

16. The method of claim 15, wherein the first needle and the second needle have a length that is at least 12 mm.

17. The method of claim 15, wherein one or a combination of transcutaneous electrical nerve stimulation, percutaneous electrical nerve stimulation, and ultrasound is used to locate the motor nerve.

18. The method of claim 15, further comprising providing a degree of skin warming throughout the delivery of the treatment.

* * * * *